US007195876B2

(12) United States Patent
Briesewitz et al.

(10) Patent No.: US 7,195,876 B2
(45) Date of Patent: Mar. 27, 2007

(54) ONCOKINASE FUSION POLYPEPTIDES ASSOCIATED WITH HYPERPROLIFERATIVE AND RELATED DISORDERS, NUCLEIC ACIDS ENCODING THE SAME AND METHODS FOR DETECTING AND IDENTIFYING THE SAME

(75) Inventors: Roger Briesewitz, Mountain View, CA (US); John H. Griffin, Atherton, CA (US)

(73) Assignee: Theravance, Inc., South San Francisco, CA (US)

( * ) Notice: Subject to any disclaimer, the term of this patent is extended or adjusted under 35 U.S.C. 154(b) by 319 days.

(21) Appl. No.: 10/637,356

(22) Filed: Aug. 8, 2003

(65) Prior Publication Data

US 2004/0045044 A1 Mar. 4, 2004

Related U.S. Application Data

(60) Provisional application No. 60/402,330, filed on Aug. 9, 2002, provisional application No. 60/440,491, filed on Jan. 16, 2003.

(51) Int. Cl.

| | |
|---|---|
| ***C12Q 1/68*** | (2006.01) |
| ***C12Q 1/48*** | (2006.01) |
| ***C12N 9/12*** | (2006.01) |
| ***C07H 21/04*** | (2006.01) |

(52) U.S. Cl. ............................ 435/6; 435/15; 435/194; 536/23.2

(58) Field of Classification Search .................... 435/6, 435/15, 194; 536/23.2

See application file for complete search history.

(56) References Cited

U.S. PATENT DOCUMENTS

| | | | | |
|---|---|---|---|---|
| 5,521,184 | A | 5/1996 | Zimmermann | |
| 5,700,822 | A * | 12/1997 | Hirth et al. | 514/380 |
| 6,258,812 | B1 | 7/2001 | Bold et al. | |
| 6,573,293 | B2 | 6/2003 | Tang et al. | |
| 2003/0171378 | A1 | 9/2003 | Griffin et al. | |

FOREIGN PATENT DOCUMENTS

WO WO 02/16351 A1 2/2002

OTHER PUBLICATIONS

Baxter et al., "The t(4;22)(q12;q11) in atypical chronic myeloid leukaemia fuses BCR to PDGFRA", Human Molecular Genetics, vol. 11, No. 12, pp. 1391-1397 (2002).

(Continued)

*Primary Examiner*—Maryam Monshipouri
(74) *Attorney, Agent, or Firm*—Jeffrey A. Hagenah; Roberta P. Saxon

(57) ABSTRACT

Oncokinase fusion polypeptides associated with hyperproliferative disorders and the polynucleotides encoding for such fusion polypeptides are provided. The fusion polypeptides have a C-terminal tyrosine kinase domain fused to an N-terminal domain that is not normally fused to the C-terminal tyrosine kinase domain and they possess constitutively activated tyrosine kinase activity. Also provided are methods for detecting and identifying the fusion polypeptides and polynucleotides and methods of diagnosing disease conditions associated with the fusion polypeptides and polynucleotides. In addition, screening assays for identifying agents useful for treating disease conditions associated with such fusion polypeptides and polynucleotides are provided. Furthermore, methods of treating disease conditions associated with the presence of the fusion polypeptides are provided.

23 Claims, 2 Drawing Sheets

OTHER PUBLICATIONS

Cools et al., "A Tyrosine Kinase Created by Fusion of the PDGFRA and FIP1L1 Genes as a Therapeutic Target of Imatinib in Idiopathic Hypereosinophilic Syndrome", The New England Journal of Medicine, vol. 348, No. 13, pp. 1201-1214 (2003).

Cross et al., "Tyrosine kinase fusion genes in chronic myeloproliferative diseases", Leukemia, vol. 16, pp. 1207-1212 (2002).

Griffin et al., "Discovery of a fusion kinase in EOL-1 cells and idiopathic hypereosinophilic syndrome", PNAS, vol. 100, No. 13, pp. 7830-7835 (2003).

Pardanani et al., "CHIC2 deletion, a surrogate for FIP1L1-PDGFRA fusion, occurs in systemic masatocytosis associated with eosinophilia and predicts response to Imatinib therapy", BLOOD First Edition Paper, published online Jul. 3, 2003; DOI 10.1182/blood-2003-05-1627.

Schaller et al., "Rapid and Complete Control of Idiopathic Hypereosinophilia with Imatinib Mesylate", Medscape General Medicine 3(3), 5 pages (2001).

* cited by examiner

4q12

EOL-1 and Patient 3

Patient 1

EOL-1 and Patient 3

Patient 1

ONCOKINASE FUSION POLYPEPTIDES ASSOCIATED WITH HYPERPROLIFERATIVE AND RELATED DISORDERS, NUCLEIC ACIDS ENCODING THE SAME AND METHODS FOR DETECTING AND IDENTIFYING THE SAME

CROSS-REFERENCE TO RELATED APPLICATIONS

Pursuant to 35 U.S.C. § 119 (e), this application claims priority to the filing date of the U.S. Provisional Patent Application Ser. No. 60/402,330 filed Aug. 9, 2002 and U.S. Provisional Patent Application Ser. No. 60/440,491 filed Jan. 16, 2003; the disclosures of which are incorporated herein by reference in their entirety.

BACKGROUND OF THE INVENTION

1. Field of the Invention

This invention is directed to novel oncokinase fusion polypeptides associated with hyperproliferative disorders and to the polynucleotides that encode for such fusion polypeptides. This invention is also directed to methods of identifying and characterizing such fusion polypeptides and polynucleotides; to methods of diagnosing disease conditions associated with such fusion polypeptides and polynucleotides; and to screening assays for identifying agents useful for treating disease conditions associated with such fusion polypeptides and polynucleotides.

2. State of the Art

An accumulation of genetic changes underlies the development and progression of hyperproliferative disorders, such as cancer, resulting in cells that differ from normal cells in their behavior, biochemistry, genetics, and microscopic appearance. Mutations in DNA that cause changes in the expression level of key proteins, or in the structures and biological activities of proteins, are thought to be at the heart of cancer. For example, cancer can be triggered when genes that play a critical role in the regulation of cell growth and survival undergo mutations that lead to their over-expression and/or activation. Such “oncogenes” are involved in the dysregulation of growth that occurs in cancers.

Kinases and phosphatases are enzymes involved in phosphorylation and dephosphorylation that help regulate many cellular activities, particularly signaling from the cell membrane to the nucleus to initiate the cell’s entrance into the cell cycle and to control other functions. For example, phosphorylation is important in signal transduction mediated by receptors via extracellular biological signals such as growth factors or hormones. Many oncogenes are kinases or phosphatases, i.e. enzymes that catalyze protein phosphorylation or dephosphorylation reactions. Kinases and phosphatases may themselves be specifically regulated by phosphorylation. A kinase or phosphatase can have its activity regulated by one or more distinct kinase or phosphatases, resulting in specific signaling cascades.

Despite a long-standing need to understand and discover methods for regulating cells involved in various disease states, the complexity of signal transduction pathways has been a barrier to the development of products and processes for such regulation. Accordingly, there is a need in the art for improved methods for detecting and modulating the activity of genes involved in signal transduction and cell cycle regulation and for treating diseases associated with cancer and related disease conditions resulting from abnormal phosphorylation activity, e.g., kinase activity.

SUMMARY OF THE INVENTION

Oncokinase, particularly tyrosine kinase, fusion polypeptides associated with hyperproliferative disorders, as well as nucleic acids encoding the same, are provided. A feature of the subject fusion polypeptides is that they include a C-terminal tyrosine kinase domain fused to an N-terminal domain that is not normally fused to the C-terminal tyrosine kinase domain, where the subject fusion polypeptides possess constitutively activated tyrosine kinase activity; i.e., they do not require the presence of an exogenous factor, e.g., a growth factor, to express their catalytic activity. The subject fusion polypeptides are further characterized in that they include at least one of the following features: (a) the C-terminal domain is from a chromosome 4 tyrosine kinase; (b) the N-terminal domain is from a chromosome 4 encoded protein, e.g., it is a NM_030917 domain; and (c) the fusion protein does not arise from a translocation event, i.e., it does not arise from the exchange of DNA between different chromosomes; where in certain embodiments, two or more, including all three of, these features are present in the subject fusion polypeptides. Also provided are methods of identifying and characterizing the subject fusion polypeptides. Also provided are methods of diagnosing disease conditions by detecting the presence of the subject polypeptides/polynucleotides and/or detecting the deletions of one or more genomic sequences, where the deletions result from the chromosomal deletion event that gives rise to the subject polypeptides/polynucleotides. In addition, screening assays for identifying agents that find use in treating disease conditions associated with the presence of the subject fusion polypeptides are provided. Furthermore, methods of treating disease conditions associated with the presence of the subject fusion polypeptides are provided.

DETAILED DESCRIPTION OF THE INVENTION

Figure 1:
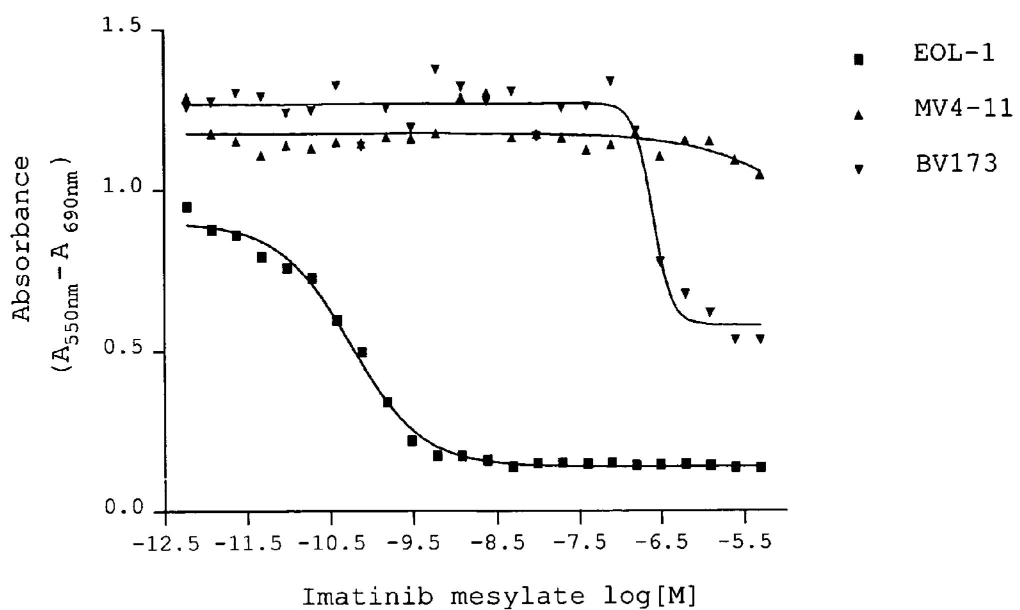
FIG. 1 shows data for a viability assay using imatinib mesylate (Gleevec™) against three leukemia cell lines.
Figure 2:
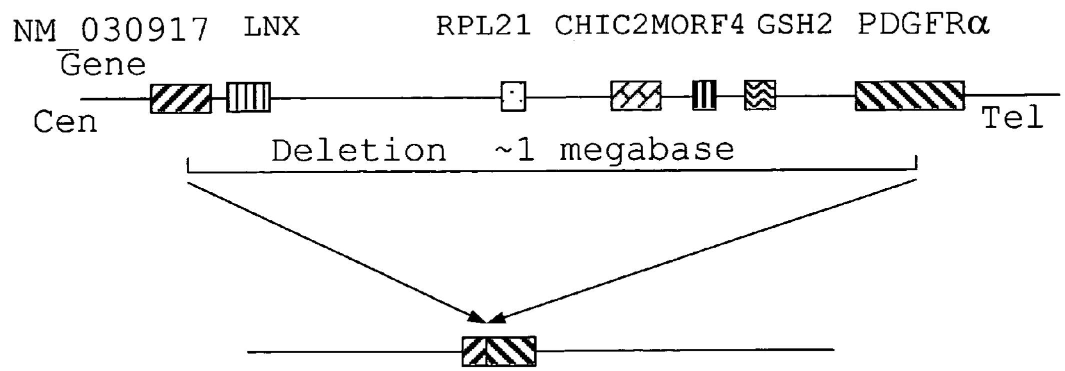
FIG. 2 provides a diagram illustrating the genetic rearrangement that gives rise to the oncogene and fusion polypeptide of the subject invention.

Oncokinase, particularly tyrosine kinase, fusion polypeptides associated with hyperproliferative disorders, as well as nucleic acids encoding the same and methods for detecting and identifying the same, are provided. A feature of the subject fusion polypeptides is that they include a C-terminal tyrosine kinase domain fused to an N-terminal domain that is not normally fused to the C-terminal tyrosine kinase domain, where the subject fusion polypeptides possess constitutively activated tyrosine kinase activity. The subject fusion polypeptides are further characterized in that they include at least one of the following features: (a) the C-terminal domain is from a chromosome 4 tyrosine kinase; (b) the N-terminal domain is from a chromosome 4 encoded protein, e.g., a NM_030917 domain; and (c) the fusion protein does not arise from a translocation event, i.e., it does not arise from the exchange of DNA between different chromosomes; where in certain embodiments, at least two of, including all three of, these features are present in the subject fusion polypeptides. Also provided are methods of identifying and characterizing the subject fusion proteins. Also provided are methods of diagnosing disease conditions by detecting the presence of the subject polypeptides/polynucleotides and/or detecting the deletions of one or more genomic sequences, where the deletions result from the chromosomal deletion event that gives rise to the subject polypeptides/polynucleotides. In addition, screening assays for identifying agents that find use in treating disease conditions associated with the presence of the subject fusion polypeptides are provided. Furthermore, methods of treating disease conditions associated with the presence of the subject fusion polypeptides are provided.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All publications mentioned herein are incorporated herein by reference for the purpose of describing and disclosing the elements that are described in the publications which might be used in connection with the presently described invention.

In further describing the subject invention, the subject oncokinase fusion polypeptide and nucleic acid compositions are described first in greater detail, followed by a more detailed review of the subject antibody, diagnostic, screening and therapeutic embodiments of the subject invention.

Oncokinase Fusion Polypeptide Compositions

As summarized above, the subject invention provides onco, particularly tyrosine, kinase fusion proteins that exhibit constitutive tyrosine kinase activity, i.e., constitutively active kinase fusion polypeptides. By constitutively active kinase activity is meant that the kinase activity is "always on," under intracellular conditions, as determined using the assay described in Science et al., (1998) 279: 577–580.

A feature of many embodiments of the subject fusion proteins is that they confer an immortalized, and often hyperproliferative, phenotype onto a cell in which they are present. In other words, cells that express the subject fusion proteins are ones that have an immortalized and often hyperproliferative phenotype. By "immortalized" is meant that the cell is immortal as determined using the assay described in Lab. Invest. (2002) 82:323–333. By "hyperproliferative" is meant that the cell divides at an above normal rate, as determined using the assay described in Cancer Cell. (2002) 1: 421–432.

The subject fusion proteins are characterized by having a C-terminal tyrosine kinase domain which is fused, either directly or through a linking domain, to an N-terminal domain that is from a different protein, i.e., is not from the same protein as the protein from which the C-terminal tyrosine kinase is obtained. In certain embodiments, the fusion of the N-terminal domain to the C-terminal tyrosine kinase domain leads to or provides for the kinase domain being constitutively active, as described above.

A further characteristic of the subject fusion polypeptides is that they also include at least one of the following features:

(1) they have a C-terminal chromosome 4 tyrosine kinase domain (i.e., a chromosome 4 encoded tyrosine kinase encoded by a coding sequence found on chromosome 4);

(2) they have an N-terminal domain of a chromosome 4 protein (i.e., a chromosome 4 encoded protein encoded by a coding sequence found on chromosome 4), e.g., NM_030917; and (3) they do not arise from a translocation event involving exchange of genetic information between different chromosomes.

In certain embodiments, the fusion polypeptides include at least two of the above features, and in certain of these embodiments the fusion peptides include all three of the above features, e.g., both the C- and N-terminal domains are from chromosome 4 encoded proteins.

By chromosome 4 tyrosine kinase is meant a tyrosine kinase whose genomic coding sequence is located on the human chromosome 4. The chromosome 4 tyrosine kinase domain of the subject fusion proteins may include a domain or portion of a number of different chromosome 4 tyrosine kinases, where representative chromosome 4 tyrosine kinases of interest include: PDGFRα, c-Kit and VEGFR-2. In many embodiments, the chromosome 4 tyrosine kinase is PDGFRα.

The fusion polypeptides of the subject invention typically include only a portion of the chromosome 4 tyrosine kinase, such that they do not include the entire coding sequence for the chromosome 4 tyrosine kinase. The portion is typically a C-terminal portion or domain of the chromosome 4 tyrosine kinase, which portion or domain exhibits kinase activity. The length of the portions or domains present in the subject fusion polypeptides is typically at least about 30% smaller, usually at least about 40% smaller and more usually at least about 50% smaller (in terms of residue number) than the full-length chromosome 4 tyrosine kinase of which it is a portion. In many embodiments, the length of the C-terminal chromosome 4 tyrosine kinase domains found in the subject fusion polypeptides is at least about 400 residues, usually at least about 450 residues and more usually at least about 500 residues, where the length of this C-terminal domain typically ranges in many embodiments from about 400 to about 1500, usually from about 500 to about 1200 and more usually from about 500 to about 1000 residues.

As summarized above, the fusion polypeptides of the present invention include an N-terminal domain of a protein that, when present in the subject fusion proteins, results in the C-terminal kinase domain being constitutively active. Accordingly, the N-terminal domain may be considered to be a kinase activating protein. The N-terminal domain is, in many embodiments, a domain of a chromosome 4 protein, where the chromosome 4 protein is typically chromosomally located within proximity to the chromosome 4 tyrosine kinase from which the C-terminal of the fusion protein is derived. Since the N-terminal chromosome 4 protein is located in proximity, the distance separating its genomic coding sequence from that of the genomic coding sequence of the tyrosine kinase typically does not exceed about 10 million base pairs, usually does not exceed about 5 million base pairs and more usually does not exceed about 3 million base pairs.

In certain embodiments, the N-terminal domain of the subject fusion polypeptides is a domain or portion of the chromosome 4 protein which is encoded by the gene with the Genbank accession no. NM_030917, i.e., a "NM_030917 protein". In some prior publications, the NM_030917 gene was identified by the Genbank accession no. BC017724. This gene has recently been named Fip1L1 (see Cools et al., *N. Eng. J. Med*. (2003) 348:1201–1214; and has also been named Rhe (See Griffin et al., *Proc. Nat'l Acad. Sci*. USA (2003) 100: 7830–7835.

The fusion polypeptides of the subject invention typically include only a portion of the chromosome 4 kinase activating protein, such that they do not include the entire amino acid sequence of the protein. The portion is typically an N-terminal portion or domain of the protein, which, when fused to a C-terminal kinase domain in the fusion protein, leads to constitutive activation of the kinase domain of the fusion protein. The length of the portions or domains present in the subject fusion polypeptides is typically at least about 1% smaller, usually at least about 5% smaller and more usually at least about 10% smaller (in terms of residue number) than the full-length chromosome 4 protein of which it is a portion. In many embodiments, the length of the N-terminal chromosome 4 kinase activating domains found in the subject fusion polypeptides is at least about 50 residues, usually at least about 100 residues and more usually at least about 200 residues, where the length of this N-terminal domain typically ranges in many embodiments from about 50 to about 350, usually from about 200 to about 350 and more usually from about 300 to about 350 residues.

The subject fusion proteins range in length from about 500 to about 2000 residues, usually from about 700 to about 1500 residues and more usually from about 800 to about 1200 amino acid residues, and the projected molecular weight of the subject proteins based solely on the number of amino acid residues in the protein ranges from about 55 to about 220, usually from about 77 to about 165 and more usually from about 88 to about 132 kDa. As the subject fusion proteins may be modified, e.g., phosphorylated, or modified in alternative ways, the actual molecular weight of these proteins may be substantially higher than the above projected molecular weights, typically ranging from about 1.1 to about 2.0 times higher than the projected molecular weight.

Of particular interest in certain embodiment are fusion proteins that have an amino acid sequence that is substantially the same as, or identical to, the sequence appearing as SEQ ID NOs: 01, 02, 03 or 04, as provided below.

By "substantially the same as" is meant a protein having a sequence that has at least about 50%, usually at least about 60% and more usually at least about 75%, and in many embodiments at least about 80%, usually at least about 90% and more usually at least about 95%, 96%, 97%, 98% or 99% sequence identity with the sequence of the above provided sequences, as measured by the BLAST compare two sequences program available on the NCBI website using default settings, as measured over the entire length of the protein, where the website has the address made up by placing "www." in front of and ".gov" in back of "ncbi.nlm.nih".

In addition to the specific fusion proteins described above, homologs or proteins (or fragments thereof from other species, i.e., other animal species, are also provided, where such homologs or proteins may be from a variety of different types of species, usually mammals, e.g., rodents, such as mice, rats; domestic animals, e.g. horse, cow, dog, cat; and primates, e.g., monkeys, baboons, humans etc. By homolog is meant a protein having at least about 35%, usually at least about 40% and more usually at least about 60% amino acid sequence identity to the specific human fusion protein as identified above, where sequence identity is determined using the algorithm described supra.

In certain embodiments, the fusion proteins of the subject invention are present in a non-naturally occurring environment, e.g., are separated from their naturally occurring environment. In certain embodiments, the subject proteins are present in a composition that is enriched for the subject proteins as compared to the subject proteins in their naturally occurring environment. As such, purified fusion proteins according to the subject invention are provided, where by purified is meant that the proteins are present in a composition that is substantially free of non-fusion proteins of the subject invention, where by substantially free is meant that less than 90%, usually less than 60% and more usually less than 50% of the composition is made up of non-fusion proteins of the subject invention.

In certain embodiments of interest, the fusion proteins are present in a composition that is substantially free of the constituents that are present in its naturally occurring environment. For example, a human fusion protein comprising a composition according to the subject invention in this embodiment will be substantially, if not completely, free of those other biological constituents, such as proteins, carbohydrates, lipids, etc., with which it is present in its natural environment. As such, protein compositions of these embodiments will necessarily differ from those that are prepared by purifying the protein from a naturally occurring source, where at least trace amounts of the constituents or other components of the protein's naturally occurring source will still be present in the composition prepared from the naturally occurring source.

The fusion proteins of the subject invention may also be present as isolates, by which is meant that the proteins are substantially free of both non-fusion proteins and other naturally occurring biologic molecules, such as oligosaccharides, polynucleotides and fragments thereof, and the like, where substantially free in this instance means that less than 70%, usually less than 60% and more usually less than 50% (by dry weight) of the composition containing the isolated fusion proteins is a non-fusion protein naturally occurring biological molecule. In certain embodiments, the fusion proteins are present in substantially pure form, where by substantially pure form is meant at least 95%, usually at least 97% and more usually at least 99% pure.

In addition to the naturally occurring proteins, polypeptides that vary from the naturally occurring proteins are also provided. By polypeptide is meant proteins having an amino acid sequence encoded by an open reading frame (ORF) of a fusion protein coding sequence, described below, including the full length protein and fragments thereof, particularly biologically active fragments and/or fragments corresponding to functional domains, and including fusions of the subject fusion proteins to yet additional proteins or parts thereof, e.g., immunoglobulin domains, peptididic tags; and the like. Fragments of interest will typically be at least about 10 aa in length, usually at least about 50 aa in length, and may be as long as 300 aa in length or longer, but will usually not exceed about 1000 aa in length.

Nucleic Acid Compositions

Also provided are nucleic acid compositions that encode the subject fusion polypeptides and fragments thereof, etc., as described above. Specifically, nucleic acid compositions encoding the subject polypeptides, as well as fragments or homologs thereof, are provided. By "nucleic acid composition" is meant a composition comprising a sequence of nucleotide bases that encodes a fusion polypeptide according to the subject invention, i.e., a region of genomic DNA capable of being transcribed into mRNA that encodes a fusion polypeptide of the subject invention, the mRNA that encodes and directs the synthesis of a fusion polypeptide of the subject invention, the cDNA derived from reverse transcription of the mRNA, etc. Specific nucleic acids of interest include those identified herein as SEQ ID NO:05; SEQ ID NO:06; SEQ ID NO:07 and SEQ ID NO:08. Also encompassed in this term are nucleic acids that are homologous, substantially similar or identical to the nucleic acids specifically disclosed herein, e.g., SEQ ID NO:05; SEQ ID NO:06; SEQ ID NO:07 and SEQ ID NO:08, where sequence similarity is determined using the BLAST compare functionality provided online by the National Center for Biotechnology (using default settings).

Also provided are nucleic acids that are homologous to the provided nucleic acids, at least with respect to the coding regions thereof. The source of homologous nucleic acids to those specifically listed above may be any mammalian species, e.g., primate species, particularly human; rodents, such as rats and mice, canines, felines, bovines, equines, etc; as well as non-mammalian species, e.g., yeast, nematodes, etc. Between mammalian species, e.g., human and mouse, homologs typically have substantial sequence similarity, e.g., at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403–10 (using default settings, i.e. parameters w=4 and T=17). Unless indicated otherwise, the sequence similarity values reported herein are those determined using the above referenced BLAST program using default settings. Of particular interest in certain embodiments are nucleic acids including a sequence substantially similar to the specific nucleic acids identified above, where by substantially similar is meant having sequence identity to this sequence of at least about 90%, usually at least about 95% and more usually at least about 99%.

Also provided are nucleic acids that hybridize to the above-described nucleic acids under stringent conditions. An example of stringent hybridization conditions is overnight incubation at 42° C. in a solution: 50% formamide, 5×SSC (750 mM NaCl, 75 mM trisodium citrate), 50 mM sodium phosphate (pH7.6), 5×Denhardt's solution, 10% dextran sulfate, and 20 μg/ml denatured, sheared salmon sperm DNA, followed by washing the filters in 0.1×SSC at about 65° C. Stringent hybridization conditions are hybridization conditions that are at least as stringent as the above representative conditions. Other stringent hybridization conditions are known in the art and may also be employed to identify nucleic acids of this particular embodiment of the invention.

Nucleic acids encoding the proteins and polypeptides of the subject invention may be cDNAs or genomic DNAs, as well as fragments thereof. The nucleic acids may also be mRNAs, e.g., transcribed from genomic DNA, that encode (i.e. are translated into) the subject proteins and polypeptides. Also provided are genes encoding the subject proteins, where the term "gene" means the open reading frame encoding specific proteins and polypeptides, and introns that are present in the open reading frame, as well as adjacent 5' and 3' non-coding nucleotide sequences involved, e.g., untranslated regions, promoter or other regulatory elements, etc., in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species or the complementary sequences thereof, where sequence elements at least include exons. Normally mRNA species have contiguous exons, with the intervening introns, when present, being removed by nuclear RNA splicing, to create a continuous open reading frame encoding an oncokinase fusion protein according to the subject invention.

A genomic sequence of interest comprises the nucleic acid present between the initiation codon and the stop codon, as defined in the listed sequences, including all of the introns that are normally present in a native chromosome. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject proteins and polypeptides, described in greater detail above. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt.

The nucleic acids of the subject invention are isolated and obtained in substantial purity, generally as other than an intact chromosome. Usually, the DNA will be obtained substantially free of other nucleic acid sequences that do not include a fusion protein sequence or fragment thereof, generally being at least about 50%, usually at least about 90% pure and are typically "recombinant," i.e. flanked by one or more nucleotides with which it is not normally associated on a naturally occurring chromosome.

In addition to the plurality of uses described in greater detail in following sections, the subject nucleic acid compositions find use in the preparation of all or a portion of the subject polypeptides, as described above.

Also provided are nucleic acid probes, as well as constructs, e.g., vectors, expression systems, etc., as described more fully below, that include a nucleic acid sequence as described above. Probes of the subject invention are generally fragments of the provided nucleic acid. The probes may be a large or small fragment, generally ranging in length from about 10 to 100 nt, usually from about 15 to 50 nt. In using the subject probes, nucleic acids having sequence similarity are detected by hybridization under low stringency conditions, for example, at 50° C. and 6×SSC (0.9 M sodium chloride/0.09 M sodium citrate)(or analogous conditions) and remain bound when subjected to washing at higher stringency conditions, e.g., 55° C. in 1×SSC (0.15 M sodium chloride/0.015 M sodium citrate) (or analogous conditions). Sequence identity may be determined by hybridization under stringent conditions, for example, at 50° C. or higher and 0.1×SSC (15 mM sodium chloride/01.5 mM sodium citrate)(or analogous conditions). Nucleic acids having a region of substantial identity to the provided nucleic acid sequences bind to the provided sequences under stringent hybridization conditions. By using probes, particularly labeled probes of DNA sequences, one can isolate homologous or related sequences.

The subject nucleic acids may be produced using any convenient protocol, including synthetic protocols, e.g., such as those where the nucleic acid is synthesized by a sequential monomeric approach (e.g., via phosphoramidite chemistry); where subparts of the nucleic acid are so synthesized and then assembled or concatamerized into the final nucleic acid, and the like. Where the nucleic acid of interest has a sequence that occurs in nature, the nucleic acid may be retrieved, isolated, amplified etc., from a natural source using conventional molecular biology protocols.

Also provided are constructs comprising the subject nucleic acid compositions, e.g., those that include a fusion protein coding sequence, inserted into a vector, where such constructs may be used for a number of different applications, including propagation, screening, genome alteration, and the like, as described in greater detail below. Constructs made up of viral and non-viral vector sequences may be prepared and used, including plasmids, as desired. The choice of vector will depend on the particular application in which the nucleic acid is to be employed. Certain vectors are useful for amplifying and making large amounts of the desired DNA sequence. Other vectors are suitable for expression in cells in culture, e.g., for use in screening assays. Still other vectors are suitable for transfer and expression in cells in a whole animal, e.g., in the production of animal models of hyperproliferative diseases. The choice of appropriate vector is well within the ability of those of ordinary skill in the art. Many such vectors are available commercially. To prepare the constructs, the partial or full-length nucleic acid is inserted into a vector typically by means of DNA ligase attachment to a cleaved restriction enzyme site in the vector. Alternatively, the desired nucleotide sequence can be inserted by homologous recombination in vivo. Typically, homologous recombination is accomplished by attaching regions of homology to the vector on the flanks of the desired nucleotide sequence. Regions of homology are added by ligation of oligonucleotides, or by polymerase chain reaction using primers that include both the region of homology and a portion of the desired nucleotide sequence, for example. Yet another means to insert the nucleic acids into appropriate vectors is to employ one of the increasingly employed recombinase based methods for transferring nucleic acids among vectors, e.g., the Creator™ system from Clontech; the Gateway™ system from Invitrogen, etc.

Also provided are expression cassettes that include a coding sequence. By expression cassette is meant a nucleic acid that includes a sequence encoding a subject peptide or protein operably linked to a promoter sequence, where by operably linked is meant that expression of the coding sequence is under the control of the promoter sequence.

Preparation of Polypeptides According to the Subject Invention

The subject fusion proteins may be obtained using any convenient protocol. As such, they may be obtained from naturally occurring sources or recombinantly produced. Naturally occurring sources of the subject proteins include tissues and portions/fractions, including cells, cell lines and fractions thereof, e.g., extracts, homogenates etc., that include cells in which the desired protein is expressed.

The subject proteins may also be obtained from synthetic protocols, e.g., by expressing a recombinant gene encoding the subject protein, such as the polynucleotide compositions described above, in a suitable host under conditions sufficient for post-translational modification to occur in a manner that provides the expressed fusion protein with the desired constitutively active kinase activity. For expression, an expression cassette may be employed. The expression cassette or vector will provide a transcriptional and translational initiation region, which may be inducible or constitutive, where the coding region is operably linked under the transcriptional control of the transcriptional initiation region, and under the translational control of the translational initiation region, and a transcriptional and translational termination region. These control regions may be native to a gene of the subject invention, or may be derived from exogenous sources.

Expression cassettes may be prepared comprising a transcription initiation region, the nucleic acid coding sequence or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the coding sequence. After introduction of the DNA, the cells containing the construct may be selected by means of a selectable marker, the cells expanded and then used for expression.

The subject proteins and polypeptides may be expressed in prokaryotes or eukaryotes in accordance with conventional ways, depending upon the purpose for expression. For large scale production of the protein, a unicellular organism, such as *E. col, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the gene in eukaryotic cells, where the encoded protein will benefit from native folding and post-translational modifications. Small peptides can also be synthesized in the laboratory. Polypeptides that are subsets of the complete sequence may be used to identify and investigate parts of the protein important for function.

Specific expression systems of interest include bacterial, yeast, insect cell and mammalian cell derived expression systems. Representative systems from each of these categories are provided below:

(i) Bacteria

Expression systems in bacteria include those described in Chang et al., *Nature* (1978) 275:615; Goeddel et al., *Nature* (1979) 281:544; Goeddel et al., *Nucleic Acids Res*. (1980) 8:4057; EP 0 036,776; U.S. Pat. No. 4,551,433; DeBoer et al., *Proc. Natl. Acad. Sci*. (*USA*) (1983) 80:21–25; and Siebenlist et al., *Cell* (1980) 20:269.

(ii) Yeast

Expression systems in yeast include those described in Hinnen et al., *Proc. Natl. Acad. Sci*. (*USA*) (1978) 75:1929; Ito et al., *J. Bacteriol*. (1983) 153:163; Kurtz et al., *mol. Cell. Biol*. (1986) 6:142; Kunze et al., *J. Basic Microbiol*. (1985) 25:141; Gleeson et al., *J. Gen. Microbiol*. (1986) 132:3459; Roggenkamp et al., *Mol. Gen. Genet*. (1986) 202:302; Das et al., *J. Bacteriol*. (1984) 158:1165; De Louvencourt et al., *J. Bacteriol*. (1983) 154:737; Van den Berg et al., *Bio/Technology* (1990) 8:135; Kunze et al., *J. Basic Microbiol*. (1985) 25:141; Cregg et al., *Mol. Cell. Biol*. (1985) 5:3376; U.S. Pat. Nos. 4,837,148 and 4,929,555; Beach and Nurse, *Nature* (1981) 300:706; Davidow et al., *Curr. Genet*. (1985) 10:380; Gaillardin et al., *Curr. Genet*. (1985) 10:49; Ballance et al., *Biochem. Biophys. Res. Commun*. (1983) 112:284–289; Tilburn et al., *Gene* (1983) 26:205–221; Yelton et al., *Proc. Natl. Acad. Sci*. (*USA*) (1984) 81:1470–1474; Kelly and Hynes, *EMBO J*. (1985) 4:475479; EP 0 244,234; and WO 91/00357.

(iii) Insect Cells

Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol*. (1988) 69:765–776; Miller et al., *Ann. Rev. Microbiol*. (1988) 42:177; Carbonell et al., *Gene* (1988) 73:409; Maeda et al., *Nature* (1985) 315:592–594; Lebacq-Verheyden et al., *Mol. Cell. Biol*. (1988) 8:3129; Smith et al., *Proc. Natl. Acad. Sci*. (*USA*) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47–55, Miller et al., *Generic Engineering* (1986) 8:277–279, and Maeda et al., *Nature* (1985) 315:592–594.

(iv) Mammalian Cells

Mammalian expression is accomplished as described in Dijkema et al., *EMBO J*. (1985) 4:761, Gorman et al., *Proc. Natl. Acad. Sci*. (*USA*) (1982) 79:6777, Boshart et al., *Cell* (1985) 41:521 and U.S. Pat. No. 4,399,216. Other features of mammalian expression are facilitated as described in Ham and Wallace, *Meth. Enz*. (1979) 58:44, Barnes and Sato, *Anal. Biochem*. (1980) 102:255, U.S. Pat. Nos. 4,767,704, 4,657,866, 4,927,762, 4,560,655, WO 90/103430, WO 87/00195, and U.S. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism.

Once the source of the protein is identified and/or prepared, e.g., a transfected host expressing the protein is prepared, the protein is then purified to produce the desired fusion protein comprising composition. Any convenient protein purification procedures may be employed, where suitable protein purification methodologies are described in Guide to Protein Purification, (Deuthser ed.) (Academic Press, 1990). For example, a lysate may be prepared from the original source, e.g. naturally occurring cells or tissues that express the subject fusion proteins or the expression host expressing the subject fusion proteins, and purified using HPLC, exclusion chromatography, gel electrophoresis, affinity chromatography, and the like.

Methods of Identifying/Characterizing Onco-Tyrosine Kinase Fusion Proteins

Also provided by the subject invention are methods for identifying and characterizing onco-tyrosine kinase fusion proteins in a sample, e.g., a cell, tissue or other sample of interest. In such methods, onco-tyrosine kinase fusion proteins are identified by first screening the sample of interest to determine whether or not any onco-tyrosine kinase fusion proteins are present in the sample. To screen a sample, tyrosine-phosphorylated proteins are typically first separated from the remaining constituents of said sample to produce a population of sample derived tyrosine phosphorylated proteins. Separation or isolation of the tyrosine-kinase fusion proteins from the remaining components in the same can be accomplished using any convenient protocol, e.g., via immunoprecipitation with an anti-phosphotyrosine antibody. Next, the constituent members of the obtained population of sample derived tyrosine phosphorylated proteins are evaluated for the presence of domains from two or more different proteins. In other words, one or more of the different proteins in the isolated population of tyrosine phosphorylated proteins are evaluated to determine whether they include domains from two or more different proteins. This evaluating step may be accomplished using any convenient protocol. In one representative embodiment, the population of tyrosine phosphorylated proteins is separated or fractionated into its constituent proteins using, for example, SDS-PAGE, 2-dimensional IE/PAGE, high-performance liquid chromatography, capillary electrophoresis, etc. Next, the constituent proteins are cleaved into smaller sized peptides, e.g., via subjection to proteolysis using an endoproteinase such as trypsin. The resultant peptides are then separated or fractionated using, for example, microbore capillary electrophoresis, high-performance liquid chromatography, or mass spectrometry. The resultant isolated or fractionated peptides are then sequenced using, for example, automated Edman degradation or mass spectrometry. The resultant sequences are then compared to the sequences of the observed peptides with known or predicted peptide sequences from proteins expressed in the organism from which the sample was obtained. Next, a determination is made as to which of the constituent proteins provides proteolysis peptides from two different proteins, for example, peptides from the N-terminal domain of the protein encoded by gene NM_030917 and peptides from the C-terminal domain of PDGFRα. In this manner, a sample of interest is screened for onco-tyrosine kinase fusion proteins.

Any identified onco-tyrosine kinase fusion proteins can be further characterized to identify one or more of: (a) the full amino acid sequence; (b) the sequence of an encoding nucleic acid, e.g., mRNA encoding the fusion protein; (c) the sequence of the gene or genomic DNA encoding the fusion protein, etc. For example, the observed peptide sequences of the identified fusion protein can be employed to design PCR primers that allow for amplification of all or part of an mRNA encoding the fusion protein, for example, the region of the mRNA that comprises the fusion junction. The resultant amplified cDNA encoding all or part of the fusion protein can then be directly sequenced or first cloned and the sequence of the cloned cDNA encoding all or part of the fusion protein determined using, for example, automated dideoxy DNA sequencing. The resultant sequence can then be used to determine the cDNA sequence to predict the sequence of a novel proteolytic peptide encompassing the fusion junction within the fusion protein. The presence of the novel proteolytic peptide encompassing the fusion junction can then be determined by for example, mass spectrometry or automated Edman degradation. The determined cDNA sequence can also be employed to design primers for amplification of genomic DNA encompassing the fusion junction. The resultant amplified genomic DNA sequence encompassing the fusion junction can then be directly sequenced or first cloned and the sequence of the cloned genomic DNA determined using, for example, automated dideoxy DNA sequencing. In this way, the identified fusion proteins are further characterized.

Antibodies

Also provided are antibodies that bind to the subject fusion proteins and homologs thereof. Suitable antibodies are obtained by immunizing a host animal with peptides comprising all or a portion of the fusion protein. Suitable host animals include rat, sheep, goat, hamster, rabbit, etc. The origin of the protein immunogen may be mouse, rat, monkey etc, but is human in many embodiments. The host animal will generally be a different species than the immunogen, e.g. human protein used to immunize rabbit, etc.

The immunogen may include the complete protein, or fragments and derivatives thereof; e.g., a fragment comprising the unique sequence found at the site of fusion of the N- and C-terminal domains. Immunogens employed in certain embodiments include all or a part of the subject fusion protein, where these residues contain any post-translation modifications, such as glycosylation, found on the native target protein. Immunogens comprising the fusion protein are produced in a variety of ways known in the art, e.g. expression of cloned genes using conventional recombinant methods, isolation from HEC, etc.

For preparation of polyclonal antibodies, the first step is immunization of the host animal with the target protein, where the target protein will preferably be in substantially pure form, comprising less than about 1% contaminant. The immunogen may include the complete target protein, fragments or derivatives thereof. To increase the immune response of the host animal, the target protein may be combined with an adjuvant, where suitable adjuvants include alum, dextran, sulfate, large polymeric anions, oil and water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies of the subject invention may be produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the human protein, the animal will generally be a hamster, guinea pig, rabbit, etc. The antibody may be purified from the hybridoma cell supernatants or ascites fluid by conventional techniques, e.g. affinity chromatography using MPTS bound to an insoluble support, protein A sepharose, etc.

The antibody may be produced as a single chain, instead of the normal multimeric structure. Single chain antibodies are described in Jost et al. (1994) *J. Biol. Chem.* 269: 26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Diagnostic Applications

Also provided are methods of diagnosing disease states associated with fusion protein activity (or even the absence thereof)(such as those disease conditions listed below), e.g., based on detecting/observing levels of fusion protein or the presence and/or expression level of the gene/coding sequence in a biological sample of interest, and/or detecting the deletions of one or more nucleic acid (particularly genomic) sequences in a sample of interest, where the deletions result from the chromosomal deletion event that gives rise to the subject polypeptides/polynucleotides.

Samples, as used herein, include biological fluids such as blood, cerebrospinal fluid, tears, saliva, lymph, dialysis fluid and the like; organ or tissue culture derived fluids; and fluids extracted from physiological tissues. Also included in the term are derivatives and fractions of such fluids. Samples may also include cells, which may be solitary or in need of being dissociated in the case of solid tissues. Alternatively tissue sections may be analyzed or a lysate of the cells may be prepared.

A number of methods are available for determining the presence and/or expression level of a gene or protein in a particular sample. For example, diagnosis may be performed by a number of methods to determine the absence or presence or altered amounts of fusion protein in a patient sample. For example, detection may utilize staining of cells or histological sections with labeled antibodies, performed in accordance with conventional methods. Cells are permeabilized to stain intracellular molecules. The antibodies of interest are added to the cell sample, and incubated for a period of time sufficient to allow binding to the epitope, usually at least about 10 minutes. The antibody may be labeled with radioisotopes, enzymes, fluorophores, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. Alternatively, the secondary antibody conjugated to a flourescent compound, e.g. fluorescein, rhodamine, Texas red, etc. The absence or presence of antibody binding may be determined by various methods, including flow cytometry of dissociated cells, microscopy, radiography, scintillation counting, etc.

Alternatively, one may focus on the presence of a gene encoding the fusion protein and/or expression of the fusion protein. A number of methods are available for analyzing nucleic acids for the presence of a specific sequence, e.g., a coding sequence for the subject fusion proteins. Where large amounts of DNA are available, genomic DNA is used directly. Alternatively, the region of interest is cloned into a suitable vector and grown in sufficient quantity for analysis. Cells that express the fusion protein may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985),. *Science* 239:487, and a review of techniques may be found in Sambrook, et al. *Molecular Cloninq: A Laboratory Manual*, CSH Press 1989, pp.14.2–14.33. Alternatively, various methods are known in the art that utilize oligonucleotide ligation as a means of detecting polymorphisms, for examples see Riley et al. (1990), *Nucl. Acids Res*. 18:2887–2890; and Delahunty et al. (1996), *Am. J. Hum. Genet*. 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two-stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g., amplified or cloned fragment, may be analyzed for variations from the specifically provided “wild type” sequences provided herein by one of a number of methods known in the art. The nucleic acid may be sequenced by dideoxy or other methods, and the sequence of bases compared to a wild-type sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for variants or mutations may be based on the functional or antigenic characteristics of the protein. Protein truncation assays are useful in detecting deletions that may affect the biological activity of the protein. Various immunoassays designed to detect polymorphisms in proteins may be used in screening. Where many diverse genetic mutations lead to a particular disease phenotype, functional protein assays have proven to be effective screening tools. The activity, e.g. kinase functionality, of the encoded protein may be determined by comparison with the wild-type protein.

Diagnostic methods of the subject invention in which the level of expression is of interest will typically involve comparison of the nucleic acid abundance of a sample of interest with that of a control value to determine any relative differences, where the difference may be measured qualitatively and/or quantitatively, which differences are then related to the presence or absence of an abnormal expression pattern. A variety of different methods for determining the nucleic acid abundance in a sample are known to those of skill in the art, where particular methods of interest include those described in: Pietu et al., *Genome Res*. (June 1996) 6: 492–503; Zhao et al., Gene (Apr. 24, 1995) 156: 207–213; Soares, Curr. Opin. Biotechnol. (October 1997) 8: 542–546; Raval, J. Pharmacol Toxicol Methods (November 1994) 32: 125–127; Chalifour et al., Anal. Biochem (Feb. 1, 1994) 216: 299–304; Stolz & Tuan, Mol. Biotechnol. (December 19960 6: 225–230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

In certain embodiments, the diagnostic applications may further include a further fusion protein characterization step, where the presence of the fusion protein of interest is found. For example, one may further characterize the particular fusion point of the fusion protein, where knowledge of the particular fusion point is of use, e.g., in developing rational treatment protocols, as described below. One may also further characterize the fusion protein to determine whether it is resistant to any particular contemplated therapeutic agent. For example, the fusion protein may include a mutation or variation as compared to the “wild-type” sequence that confers resistance to a particular pharmacological agent. A specific representative embodiment of such a mutation or alteration is the T674I mutation in the NM_030917-PDGFRα fusion protein, as described in greater detail in the experimental section, below.

In certain embodiments, instead of (or in addition to) detecting the presence of the subject fusion proteins and/or nucelci acids encoding the same, as described above, the absence of one or more nucleic acids, e.g., genomic sequences, is detected, where the absence of the one or more nucleic acids occurs because of a chromosomal deletion event that results in the presence of the subject fusion proteins, and therefore can be employed to determine the presence of the subject fusion proteins.

Specifically, since the subject fusion kinases of the present invention result from a chromosomal deletion event, one can determine the presence of the subject fusion kinases by screening or assaying for the presence of one or more particular genetic loci that are located between NM_030917 and PDGFRα and are not present if the chromosomal deletion event has occurred. Representative genomic sequences that can be assayed in these embodiments of the subject methods include sequences found in genes that are located between NM_030917 and PDGFRα, like the genes LNX, RPL21, CHIC2, MORF4 or GSH2. Alternatively, one can also assay for sequences at 4q12 that do not code for a gene, where the sequence is specific for 4q12. In yet other embodiments, one may screen for sequences at the very 3' end of NM_030917 or the 5' end of PDGFRα, including sequences coding for the extracellular domain of PDGFRα but not of sequences coding for the transmembrane of intracellular domain of PDGFRα.

In these embodiments, the presence or absence of the target sequences, as described above, can be assayed using any convenient protocol. For example, the detection of particular genetic loci can be achieved by using fluorescence in situ hybridization (FISH). In this technique, a fluorescently labeled oligonucleotide is used as a probe that will hybridize with its complementary sequence on the respective chromosome if that complementary sequence is present, which hybridization can then be detected by fluorescent microscopy. In the present situation, given that the 4q12 locus is present twice in the genetic material of each cell, hybridization of a probe derived from that region should result in two distinct hybridization events and, hence, in two fluorescent signals per normal nucleus, if no chromosomal deletion has occurred. Representative probes that can be employed include, but are not limited to: (a) those derived from genes that are located between NM_030917 and PDGFRα, such as the genes LNX, RPL21, CHIC2, MORF4 or GSH2; (b) probes derived from sequences at 4q12 that do not code for a gene; and (3) probes derived from a sequence at the very 3' end of NM_030917 or the 5' end of PDGFRα, including sequences coding for the extracellular domain of PDGFRα. If a deletion at the 4q12 locus has occurred, only one hybridization signal per nucleus will be detected. The presence of only one hybridization signal per nucleus in a significant number (e.g., at least about 100, such as about 200 or more) of hematological cells derived from the bone marrow or from peripheral blood of a patient is strongly indicative of a deletion that can have led to the formation of the fusion gene and therefore can be employed as a diagnostic marker.

Screening Assays

Also provided by the subject invention are screening protocols and assays for identifying agents that modulate, e.g., inhibit or enhance, activity of the subject fusion proteins. As such, the screening assays are assays that provide for the identification of agents that modulate, e.g., inhibit or enhance, the kinase activity of the subject fusion proteins.

The screening methods will typically be assays that provide for qualitative/quantitative measurements of fusion protein kinase activity, e.g., of the ability of the fusion protein to catalyze transfer of a phosphoryl group from a donor to an acceptor. For example, the assay could be an assay which measures the kinase activity of a fusion protein of the subject invention in the presence and absence of a candidate inhibitor agent. The screening method may be an in vitro or in vivo format, where both formats are readily developed by those of skill in the art. In other words, such assays can be done in vivo or in vitro in mammalian cells, non-mammalian cells, yeast, bacteria, etc.

A. In vitro Models of Fusion Protein Function

In vitro models of fusion protein function are provided, where the in vitro models may be cell-free models or employ the use of cells. Of particular interest are models of fusion protein kinase activity.

Cell free-models typically include: a fusion protein polypeptide and a candidate modulatory agent, e.g., competitor or inhibitor agent/molecule, where the models further typically include at least one of: a donor molecule that includes a phsohoryl group (typically ATP) that is to be transferred to an acceptor molecule and an acceptor molecule that is to receive the phosphoryl group transferred by the donor.

The competitor may be any compound that is, or is suspected to be, a compound capable of specifically inhibiting the fusion protein. Depending on the particular model, one or more of, usually one of, the specified components may be labeled, where by labeled is meant that the components comprise a detectable moiety, e.g., a fluorescent or radioactive tag, or a member of a signal producing system, e.g. biotin for binding to an enzyme-streptavidin conjugate in which the enzyme is capable of converting a substrate to a chromogenic product.

The above cell free in vitro models may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times, e.g. soluble fusion protein and a competitor ligand may be combined first, and the resultant mixture subsequently combined with bound acceptor molecule. Following the contact step, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the presence of bound fusion protein will then be detected.

In alternative in vitro models, the above components may be present in a cell free environment in which the fusion protein exhibits kinase activity in the absence of any inhibitor. The kinase activity is then monitored in the presence and absence of candidate modulating agents, where kinase activity may be determined using any convenient assay, e.g., the kinase activity assay described in Proc. Nat'l Acad. Sci. USA (2002) 97:2419–2424.

Also of interest are in vitro models in which cells are employed. There are numerous cell containing in vitro assays which can be readily adapted by those of skill in the art for the purposes described herein. For example, the activity of an inhibitor of the subject oncokinase fusion polypeptides can be assessed biochemically using cells expressing the oncogene. Those cells can be a cancer cell line or they can be a cell line generated from the transfection of fusion kinase cDNA. As a reflection of its constitutive activity, fusion kinase polypeptide autophosphorylates. If cells are incubated with an inhibitor, the level of kinase inhibition can be evaluated by immunoprecipitating the fusion kinase polypeptide and subsequently, by performing a Western Blot analysis in which the blotting antibody is selective for phosphotyrosine residues. The level of kinase inhibition is reflected in the decrease of tyrosine phosphorylation of the fusion kinase polypeptide.

In another embodiment, the inhibition of the fusion kinase polypeptide with an inhibitor leads to cellular responses in the respective primary cancer cells and cancer cell lines or appropriate cell lines derived from the transfection of the fusion kinase polypeptide cDNA. The cellular responses can include decreased proliferation, differentiation or apoptosis. The inhibition of proliferation can be assessed by a multitude of assays, including simple cell counting as well as incorporation of BrdU into DNA followed by ELISA. Induction of apoptosis can be evaluated by annexin staining using flow cytometry, assays for the functional integrity of mitochondria (MTT assays) as well as assays to monitor caspase activation or DNA fragmentation.

B. In Vivo Models of Fusion Protein Function

A variety of different in vivo models of fusion protein function are also provided by the subject invention and may be used in the screening assays of the subject invention. In vivo models of interest include engineered cells that include an expression cassette encoding the subject fusion proteins. Also of interest in the subject screening assays are multicellular in vivo models, e.g., the transgenic animal models described below.

The subject nucleic acids can be used to generate transgenic, non-human animals or site-specific gene modifications in cell lines. Transgenic animals may be made through homologous recombination, where the normal locus is altered. Alternatively, a nucleic acid construct is randomly integrated into the genome. Vectors for stable integration include plasmids, retroviruses and other animal viruses, YACs, and the like.

The modified cells or animals are useful in the study of fusion protein function and regulation. Specific constructs of interest include anti-sense, which will block expression, expression of dominant negative mutations, and over-expression of fusion protein genes. Where a sequence is introduced, the introduced sequence may be either a complete or partial sequence of a gene that is exogenous to the host animal, e.g., a human sequence. A detectable marker, such as lac Z, may be introduced into the locus, where upregulation of expression will result in an easily detected change in phenotype.

One may also provide for expression of the gene or variants thereof in cells or tissues where it is not normally expressed (e.g., mammalian, non-mammalian, yeast, bacterial, etc. cells), at levels not normally present in such cells or tissues, or at abnormal times of development. DNA constructs for homologous recombination will comprise at least a portion of the gene native to the species of the host animal, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on fusion protein activity.

Also of interest are assays involving xenotransplants of hyperproliferative cells and cell lines into immunocompromised host animals, e.g., mice, where cellular, e.g., tumor, growth is identified as a readout of the inhibition of the fusion protein by a candidate agent being screened.

Typical in vivo cancer models for solid tumors involve the grafting of a piece of primary human tumor or, more frequently, of cells from a human tumor cell line onto immunocompromised mice like nude, SCID or NOD/SCID mice. The human tumor cells engraft, either subcutaneously or in a target organ. If the engraftment takes place subcutaneously, tumor growth can be followed and recorded based on size. In order to demonstrate activity of an anti-cancer compound, the engrafted mice are treated with the compound and the reduction in size of the tumor is recorded and/or the prolongation of the survival of the mice is followed.

Assays of interest for fluid or liquid tumors, e.g., leukemias, include the following:

1) Subcutaneous injection of a liquid tumor cell line into an immunocompromised host animal, e.g., NOD/SCID mice. Although being a liquid tumor, the tumor cells can form a solid tumor subcutaneously in an immunocompromised host. Once the solid tumor has reached a certain size, administration of the candidate agent starts and activity of the candidate agent is measured in reduction of tumor size and survival.

2) Injection of a cell line (e.g., BaF3 based) expressing the fusion kinase into a host animal, e.g., into the tail vein of a suitable syngeneic mouse (Balb c). The injected cells proliferate in the blood of the animal, accumulate in the spleen and eventually kill the host animal due to organ damage. The weight of the spleen and the time of survival following administration of a given candidate agent serves as an indicator for the success of the therapeutic to affect the cancer.

3) Transduction of bone marrow stem cells with a retrovirus that leads to the expression of a mutant kinase. As a result of the expression of the mutant kinase in hematopoietic stem cells, the cells proliferate in an unregulated way which eventually kills the host animal, e.g., mouse, in which they are present. A candidate agent that inhibits the transduced activated kinase and prolongs the survival of the host animal is one that exhibits activity against the target fusion oncokinase polypeptide.

Whether the format is in vivo or in vitro, the model being employed is combined with the candidate agent and the effect of the candidate agent on the model is observed and related to the modulatory activity of the agent being tested. For example, for screening inhibitory agents, the model is combined with the candidate agent in an environment in which, in the absence of the candidate agent, kinase activity is observed. The conditions may be set up in vitro by combining the various required components in an aqueous medium, or the assay may be carried out in vivo, etc.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. A preferred class of candidate agents includes those that mimic ATP, the co-substrate for the phosphoryl transfer reaction catalyzed by the fusion proteins. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents identified in the above screening assays that inhibit activity of the subject fusion proteins find use in various methods, where representative methods are described below.

Methods of Modulating Fusion Protein Activity

Also provided by the subject invention are methods of modulating, including enhancing and repressing, the activity of the subject fusion proteins. As such, methods of both increasing and decreasing fusion protein kinase activity are provided. In many embodiments, such methods are methods of inhibiting fusion protein kinase activity.

One representative method of inhibiting fusion protein activity is to employ small molecules that inhibit the fusion protein activity. Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs (especially of ATP) or combinations thereof. Such molecules may be identified, among other ways, by employing the screening protocols described above.

In yet other embodiments, expression of the target fusion protein is inhibited. Inhibition of target fusion protein expression may be accomplished using any convenient means, including administration of an agent that inhibits target fusion protein expression (e.g., antisense agents), inactivation of the encoding gene, e.g., through recombinant techniques, etc.

Antisense molecules can be used to down-regulate expression of the target protein in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g., by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol*. 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-$CH_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International Patent Application WO 95/23225, and Beigelman et al. (1995), *Nucl. Acids Res*. 23:4434–42). Examples of oligonucleotides with catalytic activity are described in WO 95/06764. Conjugates of anti-sense ODN with a met al complex, e.g. terpyridylCu(II), capable of mediating mRNA hydrolysis are described in Bashkin et al. (1995), *Appl. Biochem. Biotechnol*. 54:43–56.

In another embodiment, the target protein gene is inactivated so that it no longer expresses the target fusion protein. By inactivated is meant that the gene, e.g., coding sequence and/or regulatory elements thereof, is genetically modified so that it no longer expresses a protein, or at least a functional protein. The alteration or mutation may take a number of different forms, e.g., through deletion of one or more nucleotide residues in the fusion protein region, through exchange of one or more nucleotide residues in the fusion protein region, and the like. One means of making such alterations in the coding sequence is by homologous recombination. Methods for generating targeted gene modifications through homologous recombination are known in the art, including those described in: U.S. Pat. Nos. 6,074,853; 5,998,209; 5,998,144; 5,948,653; 5,925,544; 5,830,698; 5,780,296; 5,776,744; 5,721,367; 5,614,396; 5,612,205; the disclosures of which are herein incorporated by reference.

The above-described methods of inhibiting fusion protein activity find use in a number of different applications. In many applications, the subject methods and compositions are employed to inhibit fusion protein activity in a cell that endogenously comprises a coding sequence for the target fusion protein. Expression of the target gene is considered to be inhibited if, consistent with the above description, expression is decreased by at least about 2 fold, usually at least about 5 fold and often by at least about 25, about 50, about 100 fold or more, as compared to a control, e.g., an otherwise identical cell not subjected to the subject methods.

A more specific application in which the subject methods find use is to decrease the proliferative capacity of a cell. The term "proliferative capacity" as used herein refers to the number of divisions that a cell can undergo, and preferably to the ability of the target cell to continue to divide. The subject methods typically result in a decrease in proliferative capacity of at least about 1.2–2 fold, usually at least about 5 fold and often at least about 10, 20, 50 fold or even higher, compared to a control.

Another specific application in which the subject methods find use is to induce apoptosis, or programmed cell death, in a cell. The subject methods typically result in a decrease in the viable cell counts of at least 20%, usually at least 50%, and often of at least 90% or even higher.

Therapeutic Applications of Fusion Protein Activity Modulation

The methods also find use in a variety of therapeutic applications in which it is desired to modulate, e.g., increase or decrease, and typically decrease, fusion protein kinase activity in a target cell or collection of cells, where the collection of cells may be a whole animal or portion thereof, e.g., tissue, organ, etc. As such, the target cell(s) may be a host animal or portion thereof. In such methods, an effective amount of an active agent that modulates fusion protein activity, e.g., enhances or decreases oncokinase activity as desired, is administered to the target cell or cells, e.g., by contacting the cells with the agent, by administering the agent to the animal, etc. By effective amount is meant a dosage sufficient to modulate fusion protein activity in the target cell(s), as desired.

A variety of different types of agents may be employed, including the representative types of candidate agents described above, e.g., small molecule agents, nucleic acid agents, polypeptide agents, etc.

In certain embodiments, the agents are pyrimidine derivatives as described in U.S. Pat. No. 5,521,184, the disclosure of which is herein incorporated by reference. In these embodiments, of interest are N-phenyl-2-pyrimidine-amine derivatives of formula (I):

(I)

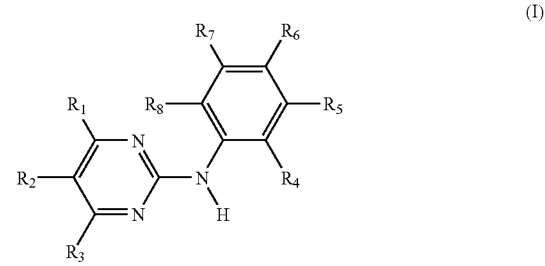

wherein $R_1$ is 4-pyrazinyl, 1-methyl-1H-pyrrolyl, amino- or amino-lower alkyl-substituted phenyl wherein the amino group in each case is free, alkylated or acylated, 1H-indolyl or 1H-imidazolyl bonded at a five-membered ring carbon atom, or unsubstituted or lower alkyl-substituted pyridyl bonded at a ring carbon atom and unsubstituted or substituted at the nitrogen atom by oxygen, $R_2$ and $R_3$ are each independently of the other hydrogen or lower alkyl, one or two of the radicals $R_4$, $R_5$, $R_6$, $R_7$ and $R_8$ are each nitro, fluoro-substituted lower alkoxy or a radical of formula (II):

$$—N(R_9)—C(=X)—(Y)_k—R_{10} \quad \text{(II)}$$

wherein $R_9$ is hydrogen or lower alkyl,

X is oxo (O), thio (S), imino (NH), N-lower alkyl-imino, hydroximino or O-lower alkyl-hydroximino, Y is oxygen or the group NH, k is 0 or 1 and $R_{10}$ is an aliphatic radical having at least 5 carbon atoms, or an aromatic, aromatic-aliphatic, cycloaliphatic, cycloaliphatic-aliphatic, heterocyclic or heterocyclic-aliphatic radical, and the remaining radicals $R_4$, $R_5$, $R_6$, $R_7$ and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterifed hydroxy, free, alkylated or acylated amino or free or esterified carboxy, and salts of such compounds having at least one salt-forming group.

In these embodiments:

1-Methyl-1H-pyrrolyl is preferably 1-methyl-1H-pyrrol-2-yl or 1-methyl-1H-pyrrol-3-yl.

Amino- or amino-lower alkyl-substituted phenyl $R_1$ wherein the amino group in each case is free, alkylated or acylated, is phenyl substituted in any desired position (ortho, meta or para) wherein an alkylated amino group is preferably mono- or di-lower alkylamino, for example dimethylamino, and the lower alkyl moiety of amino-lower alkyl is preferably linear $C_1$–$C_3$ alkyl, such as especially methyl or ethyl.

1H-lndolyl bonded at a carbon atom of the five-membered ring is 1H-indol-2-yl or 1H-indol-3-yl.

Unsubstituted or lower alkyl-substituted pyridyl bonded at a ring carbon atom is lower alkyl-substituted or preferably unsubstituted 2-, or preferably 3- or 4-pyridyl, for example 3-pyridyl, 2-methyl-3-pyridyl, 4-methyl-3-pyridyl or 4-pyridyl. Pyridyl substituted at the nitrogen atom by oxygen is a radical derived from pyridine N-oxide, i.e. N-oxido-pyridyl, e.g. N-oxido-4-pyridyl.

Fluoro-substituted lower alkoxy is lower alkoxy carrying at least one, but preferably several, fluoro substituents, especially trifluoromethoxy or preferably 1,1,2,2-tetrafluoro-ethoxy.

When X is oxo, thio, imino, N-lower alkyl-imino, hydroximino or O-lower alkyl-hydroximino, the group C═X is, in the above order, a radical C═O, C═S, C═N—H, C═N-lower alkyl, C═N—OH or CN—O-lower alkyl, respectively. X is preferably oxo.

k is preferably 0, i.e. the group Y is not present.

Y, if present, is preferably the group NH.

The term “lower” within the scope of this text denotes radicals having up to and including 7, preferably up to and including 4 carbon atoms.

Lower alkyl $R_1$, $R_2$, $R_3$ and $R_9$ is preferably methyl or ethyl.

An aliphatic radical $R_{10}$ having at least 5 carbon atoms preferably has not more than 22 carbon atoms, generally not more than 10 carbon atoms, and is such a substituted or preferably unsubstituted aliphatic hydrocarbon radical, that is to say such a substituted or preferably unsubstituted alkynyl, alkenyl or preferably alkyl radical, such as $C_5$–$C_7$ alkyl, for example n-pentyl. An aromatic radical $R_{10}$ has up to 20 carbon atoms and is unsubstituted or substituted, for example in each case unsubstituted or substituted naphthyl, such as especially 2-naphthyl, or preferably phenyl, the substituents preferably being selected from cyano, unsubstituted or hydroxy-, amino- or 4-methyl-piperazinyl-substituted lower alkyl, such as especially methyl, trifluoromethyl, free, etherified or esterified hydroxy, free, alkylated or acylated amino and free or esterified carboxy. In an aromatic-aliphatic radical $R_{10}$ the aromatic moiety is as defined above and the aliphatic moiety is preferably lower alkyl, such as especially $C_1$–$C_2$ alkyl, which is substituted or preferably unsubstituted, for example benzyl. A cycloaliphatic radical $R_{10}$ has especially up to 30, more especially up to 20, and most especially up to 10 carbon atoms, is mono-or poly-cyclic and is substituted or preferably unsubstituted, for example such a cycloalkyl radical, especially such a 5- or 6-membered cycloalkyl radical, such as preferably cyclohexyl. In a cycloaliphatic-aliphatic radical $R_{10}$ the cycloaliphatic moiety is as defined above and the aliphatic moiety is preferably lower alkyl, such as especially $C_1$–$C_2$ alkyl, which is substituted or preferably unsubstituted. A heterocyclic radical $R_{10}$ contains especially up to 20 carbon atoms and is preferably a saturated or unsaturated monocyclic radical having 5 or 6 ring members and 1–3 hetero atoms which are preferably selected from nitrogen, oxygen and sulfur, especially, for example, thienyl or 2-, 3- or 4-pyridyl, or a bi- or tri-cyclic radical wherein, for example, one or two benzene radicals are annellated (fused) to the mentioned monocyclic radical. In a heterocyclic-aliphatic radical $R_{10}$ the heterocyclic moiety is as defined above and the aliphatic moiety is preferably lower alkyl, such as especially $C_1$–$C_2$ alkyl, which is substituted or preferably unsubstituted.

Etherified hydroxy is preferably lower alkoxy. Esterified hydroxy is preferably hydroxy esterified by an organic carboxylic acid, such as a lower alkanoic acid, or a mineral acid, such as a hydrohalic acid, for example lower alkanoyloxy or especially halogen, such as iodine, bromine or especially fluorine or chlorine.

Alkylated amino is, for example, lower alkylamino, such as methylamino, or di-lower alkylamino, such as dimethylamino. Acylated amino is, for example, lower alkanoylamino or benzoylamino.

Esterified carboxy is, for example, lower alkoxycarbonyl, such as methoxycarbonyl.

A substituted phenyl radical may carry up to 5 substituents, such as fluorine, but especially in the case of relatively large substituents is generally substituted by only from 1 to 3 substituents. Examples of substituted phenyl that may be given special mention are 4-chloro-phenyl, pentafluoro-phenyl, 2-carboxy-phenyl, 2-methoxy-phenyl, 4-fluorophenyl, 4-cyano-phenyl and 4-methyl-phenyl.

Salt-forming groups in a compound of formula (I) are groups or radicals having basic or acidic properties. Compounds having at least one basic group or at least one basic radical, for example a free amino group, a pyrazinyl radical or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed.

Compounds of formula (I) having acidic groups, for example a free carboxy group in the radical $R_{10}$, may form met al or ammonium salts, such as alkali met al or alkaline earth met al salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethylpiperidine or N,N'-dimethyl-piperazine.

Compounds of formula (I) having both acidic and basic groups can form internal salts.

Of particular interest in these embodiments is a pyrimidine derivative described in this patent in which $R_1$ is 3-pyridyl, $R_2$, $R_3$, $R_5$, $R_6$, and $R_8$ are each hydrogen, $R_4$ is methyl, and $R_7$ is a group of formula (II) in which $R_9$ is hydrogen, X is oxo, k is 0, and $R_{10}$ is 4-[(4-methyl-1-piperazinyl)methyl]phenyl. The mesylate salt of this compound having the chemical name 4-[(4-methyl-1-piperazinyl)methyl]-N-[4-methyl-3-[[4-(3-pyridinyl)-2-pyrimidinyl]amino-phenyl]benzamide methanesulfonate is now commonly known as imatinib mesylate and sold under the trademark Gleevec™.

In yet other embodiments of interest, the agent is not imatinib mesylate.

Also of interest are phthalazine compounds of formula (III):

(III)

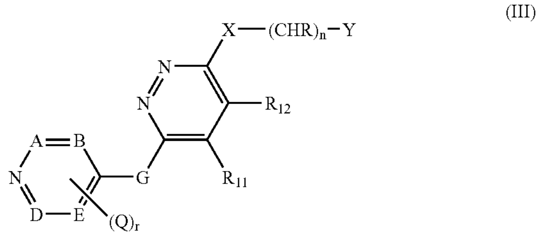

wherein r is 0 to 2, n is 0 to 2; m is 0 to 4; $R_{11}$ and $R_{12}$ (i) are in each case a lower alkyl, or (ii) together form a bridge in subformula (III*)

(III*)

(Z)m or (iii) together form a bridge in subformula (III**):

(III**)

$T_1$ $T_2$ $T_3$ $T_4$ wherein one or two of the ring members $T_1$, $T_2$, $T_3$, and $T_4$ are nitrogen, and the remainder are in each case CH; A, B, D, and E are N or CH, wherein not more than 2 of these radicals are N; G is lower alkylene, acyloxy- or hydroxy-lower alkylene, —$CH_2$—O—, —$CH_2$—S—, —$CH_2$—NH—, oxa, thia, or imino; Q is lower alkyl, especially methyl; R is H or lower alkyl; X is imino, oxa, or thia; Y is aryl, pyridyl, or (un)substituted cycloalkyl; and Z is independently mono- or disubstituted amino, halogen, alkyl, substituted alkyl, hydroxy, etherified or esterified hydroxy, nitro, cyano, carboxy, esterified carboxy, alkanoyl, carbamoyl, N-mono- or N,N-disubstituted carbamoyl, amidino, guanidino, mercapto, sulfo, phenylthio, phenyl-lower alkylthio, alkylphenylthio, phenylsulfinyl, phenyl-lower alkylsulfinyl, alkylphenylsulfinyl, phenylsulfonyl, phenyl-lower alkylsulfonyl, or alkylphenylsulfonyl; and wherein the dashed lines independently represent optional double bonds; or an N-oxide of said compound with the stipulation that, if Y is pyridyl or unsubstituted cycloalkyl, X is imino, and the remaining radicals are as defined, then G is selected from the group comprising lower alkylene, —$CH_2$—O—, —$CH_2$—S—, oxa and thia; or a salt thereof. Such compounds, e.g., PTK787 (also known as Vatalanib), are further described in WO 98/35958, U.S. patent application Ser. No. 09/859858, and U.S. Pat. No. 6,258,812 B1; the disclosure of the latter of which is herein incorporated by reference.

Also of interest in certain embodiments are the protein tyrosine kinase inhibitors of formula (IV):

(IV)

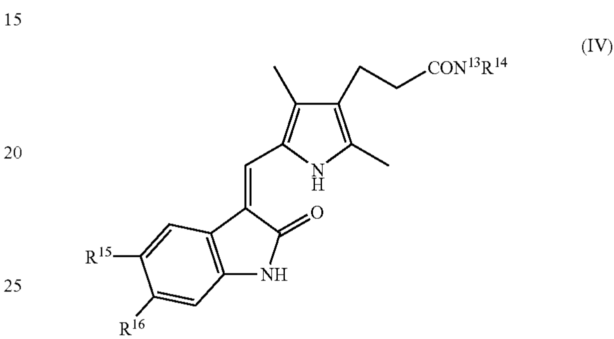

in which:

(i) $R^{13}$ represents a hydrogen atom or a $C_{1-4}$alkyl group; and $R^{14}$ represents a group of formula —$A^1$—$NR^{17}R^{18}$ in which each of $R^{17}$ and $R^{18}$ independently represents a hydrogen atom or a $C_{1-4}$alkyl group and $A^1$ represents $(CH_2)_{m'}$, $(CH_2)_{n'}$—$A^2$—$(CH_2)_{p'}$, or $(CH_2CH_2O)_{q'}CH_2CH_2$ in which m' is an integer of from 2 to 10, each of n' and p' is an integer of from 1 to 6, $A^2$ is CH═CH, phenylene, biphenylene, cyclohexylene or piperazinylene and q' is 1, 2 or 3;

(ii) $R^{13}$ and $R^{14}$ together represent —$A^3$—$NR^{19}$—$A^4$— in which each of $A^3$ and $A^4$ independently represents $(CH_2)_{r'}$ or $(CH_2CH_2O)_{s'}CH_2CH_2$ in which r' is an integer of from 2 to 6, s' is 1, 2 or 3, and $R^{19}$ represents a hydrogen atom or a $C_{1-4}$alkyl group;

(iii) $R^{13}$ and $R^{14}$ together with the nitrogen atom to which they are attached represent a piperidinyl group, which piperidinyl group bears a substituent of formula —$A^5$—$R^{20}$ at the 4 position, in which $A^5$ represents $C_{1-4}$alkylene and $R^{20}$ represents piperidin-4-yl; or (iv) $R^{13}$ and $R^{14}$ together with the nitrogen atom to which they are attached represent a pyrrolidinyl, piperidinyl or morpholino group; and $R^{15}$ and $R^{16}$ each independently represents a hydrogen atom, a halogen atom, a $C_{1-4}$alkyl group, a $C_{1-4}$alkoxy group, a phenyl group which is unsubstituted or substituted by one or two substituents selected independently from a halogen atom, a $C_{1-4}$alkyl group and a $C_{1-4}$alkoxy group, a group of formula $R^{21}S(O)_2NR^{22}$—, a group of formula $R^{23}N(R^{24})S(O)_2$—, a group of formula $R^{25}C(O)N(R^{26})$— or a group of formula $R^{27}N(R^{28})C(O)$— in which each of $R^{21}$, $R^{23}$, $R^{25}$ and $R^{27}$ independently represents a $C_{1-4}$alkyl group or a phenyl group which is unsubstituted or substituted by one or two substituents selected independently from a halogen atom, a $C_{1-4}$alkyl group and a $C_{1-4}$alkoxy group, and each of $R^{22}$, $R^{24}$, $R^{26}$ and $R^{28}$ independently represents a hydrogen atom or a $C_{1-4}$alkyl group;

or a pharmaceutically-acceptable salt thereof.

An inhibitor of formula (IV) of particular interest, identified as THRX-165724, is one in which $R^{13}$ and $R^{14}$ and the nitrogen to which they are attached form a piperazinyl ring and $R^{15}$ and $R^{16}$ are both hydrogen. Compounds of formula (IV) are described in U.S. patent application Ser. Nos. 60/343,746, 60/343,813, and Ser. No. 10/327,385, the disclosures of which are herein incorporated by reference.

Another group of compounds of interest in certain embodiments are compounds of formula (V):

(V)

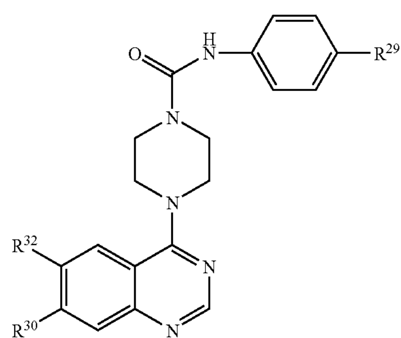

wherein:

$R^{29}$ is selected from the group consisting of —CN, —X, —$CX_3$, —$R^{33}$, —$CO_2R^{33}$, —$SO_2R^{33}$, —O—$C_{1-8}$alkyl that is straight or branched chained, —O-phenyl, —O-napthyl, —O-indolyl, and —O-isoquinolinyl, in which X is a halogen, and $R^{33}$ is hydrogen or a $C_{1-8}$alkyl that is straight or branched chained, $R^{30}$ and $R^{32}$ are each independently selected from the group consisting of —O—$CH_3$, —O—$CH_2$—$CH_3$, —O—$CH_2$—CH=$CH_2$, —O—$CH_2$—C≡CH, —O($CH_2$)—$SO_2$—$R^{33}$, —O—$CH_2$—CH($R^{34}$)$CH_2$—$R^{31}$ and —O(—$CH_2$)$_{n''}$—$R^{31}$, in which $R^{34}$ is —OH, —X, or a $C_{1-8}$alkyl that is straight or branched chained, n" is 2 or 3, and $R^{31}$ is selected from the group consisting of; —OH, —O—$CH_3$, —O—$CH_2$—$CH_3$, —$NH_2$, —N(—$CH_3$)$_2$, —NH—$CH_2$-phenyl, —NH-phenyl, —CN, —C(=NH)—$NH_2$, —NH—C(=NH)—$NH_2$, thiazolyl, oxazolyl, pyrrolidinyl, 4,4-difluoropiperidinyl, 3,3,-difluoropiperidinyl, 3,3-difluoropyrrolidinyl, morpholinyl, piperidinyl, imidazolyl, 1,2,3,-triazolyl, methylpiperidinyl, thiomorpholinyl 1,1-dioxide-thiomorpholinyl, —O-4-pyridinyl, 1H-tetrazolyl, piperazinyl, and 4-methylpiperazinyl; and pharmaceutically-acceptable isomers, salts, hydrates, solvates, and prodrug derivatives thereof.

Among compounds of formula (V), of particular interest is the compound, identified as MLN518 in which $R^{29}$ is —O-isopropyl, $R^{30}$ is —O—($CH_2$)$_3$-piperidin-1-yl, and $R^{32}$ is —$OCH_3$. Compounds of formula (V) are further described in WO 02/16351, which is incorporated herein by reference.

Yet another group of compounds of interest in certain embodiments are compounds of formula (VI):

(VI)

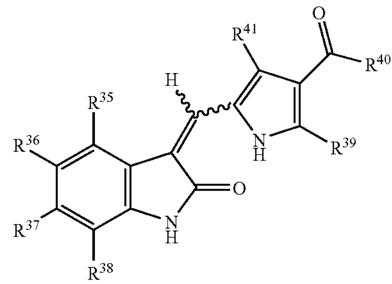

wherein:

$R^{35}$ is selected from the group consisting of hydrogen, halo, alkyl, cycloalkyl, aryl, heteroaryl, heteroalicyclic, hydroxy, alkoxy, —C(O)$R^{48}$, —$NR^{46}R^{47}$, —($CH_2$)$_{r*}R^{49}$ and —C(O)$NR^{42}R^{43}$;

$R^{36}$ is selected from the group consisting of hydrogen, halo, alkyl, trihalomethyl, hydroxy, alkoxy, cyano, —$NR^{46}R^{47}$, —$NR^{46}$C(O)$R^{47}$, —C(O)$R^{48}$, aryl, heteroaryl, and —S(O)$_2NR^{46}R^{47}$;

$R^{37}$ is selected from the group consisting of hydrogen, halo, alkyl, trihalomethyl, hydroxy, alkoxy, —C(O)$R^{48}$, —$NR^{46}R^{47}$, aryl, heteroaryl, —$NR^{46}$S(O)$_2R^{47}$, —S(O)$_2NR^{46}R^{47}$, —$NR^{46}$C(O)$R^{47}$, —$NR^{46}$C(O)O$R^{47}$, and —S(O)$_2R^{53}$, wherein $R^{53}$ is alkyl, aryl, aralkyl, heteroaryl or heteroaralkyl;

$R^{38}$ is selected from the group consisting of hydrogen, halo, alkyl, hydroxy, alkoxy, and —$NR^{46}R^{47}$;

$R^{39}$ is selected from the group consisting of hydrogen, alkyl and —C(O)$R^{40}$;

$R^{41}$ is selected from the group consisting of hydrogen, alkyl, aryl, heteroaryl, —C(O)$R^{50}$ and —C(O)$R^{40}$;

$R^{42}$ and $R^{43}$ are independently selected from the group consisting of hydrogen, alkyl and aryl;

$R^{40}$ is selected from the group consisting of hydroxy, alkoxy, aryloxy, —N($R^{44}$)($CH_2$)$_{n*}R^{45}$, and —$NR^{46}R^{47}$;

$R^{44}$ is selected from the group consisting of hydrogen and alkyl;

$R^{45}$ is selected from the group consisting of —$NR^{46}R^{47}$, hydroxy, —C(O)$R^{48}$, aryl, heteroaryl, —$N^+(O^-)R^{46}R^{47}$, —N(OH)$R^{46}$, and —NHC(O)$R^a$, wherein $R^a$ is unsubstituted alkyl, haloalkyl, or aralkyl;

$R^{46}$ and $R^{47}$ are independently selected from the group consisting of hydrogen, alkyl, lower alkyl substituted with hydroxyalkylamino, cyanoalkyl, cycloalkyl, aryl, and heteroaryl; or $R^{46}$ and $R^{47}$ may combine to form a heterocyclo group;

$R^{48}$ is selected from the group consisting of hydrogen, hydroxy, alkoxy, and aryloxy;

$R^{49}$ is selected from the group consisting of hydroxy, —C(O)$R^{48}$, —$NR^{46}R^{47}$ and —C(O)$NR^{46}R^{47}$;

$R^{50}$ is selected from the group consisting of alkyl, cycloalkyl, aryl and heteroaryl; and n* and r* are independently 1, 2, 3, or 4; or a pharmaceutically-acceptable salt thereof.

A compound of formula (VI) of particular interest, identified as SU11248, is the compound in which $R^{36}$ is fluoro, $R^{35}$, $R^{37}$, and $R^{38}$ are each hydrogen, $R^{39}$ and $R^{41}$ are each methyl, and $R^{40}$ is —N(H)($CH_2$)$_2$N($C_2H_5$)$_2$. Compounds of formula (VI) are described in WO 01/60814, the disclosure of which is incorporated herein by reference.

In one embodiment, the agent employed in the methods of this invention is selected from the group consisting of:

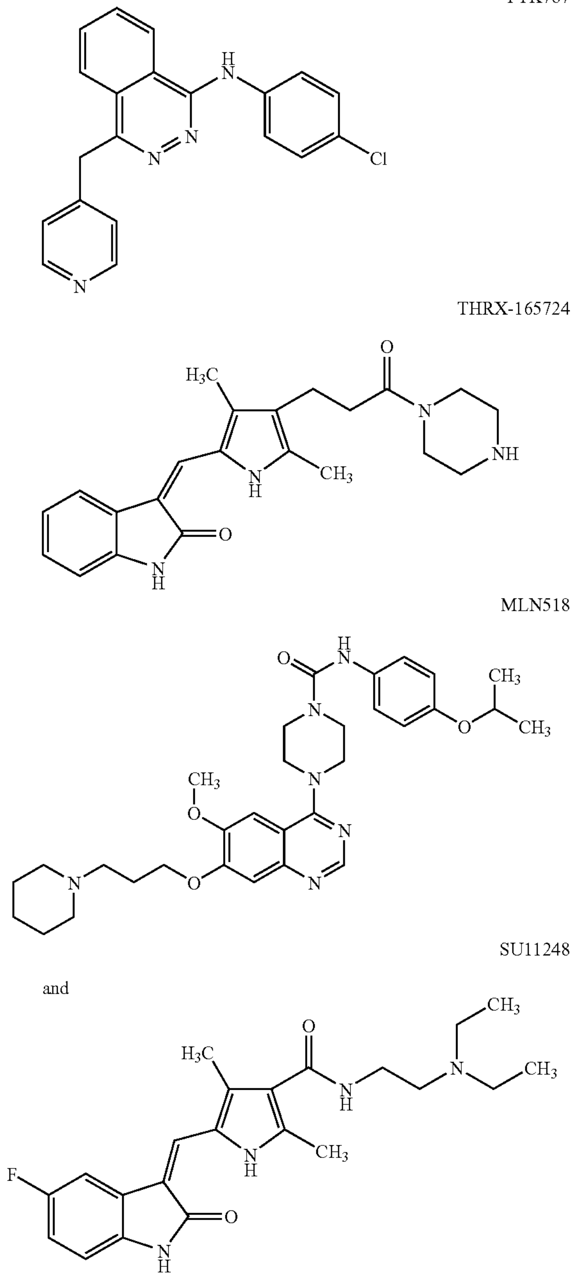

or a pharmaceutically-acceptable salt thereof.

Also of interest are other protein tyrosine kinase inhibitors. Such inhibitors include, but are not limited to, the tyrosine kinase inhibitors appearing in Appendix A of the priority provisional applications having Ser. Nos. 60/402,330 filed on Aug. 9, 2002 and 60/440,491 filed on Jan. 16, 2003; the disclosures of which are herein incorporated by reference.

In the subject methods, the active agent(s) may be administered to the targeted cells using any convenient means capable of resulting in the desired modulation of fusion protein activity. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intratracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols; which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Where the agent of interest is imatinib mesylate, the dosage employed in certain embodiments is substantially less than that which is employed for the use of imatinib mesylate in the treatment of chronic myeloid leukemia (CML). By substantially less is meant at least about 2-fold, usually at least about 3-fold and more usually at least about 4-fold less than the dosages employed in the treatment of CML, where typical dosages of imatinib mesylate employed in the subject methods may range from about 30 mg/day to about 300 mg/day, usually from about 50 mg/day to about 200 mg/day. In yet other embodiments, the dosage employed is the same as or greater than that employed in the treatment of CML. The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The invention further provdes a process for producing a pharmaceutical composition comprising a pharmaceutically acceptable carrier and an agent that inhibits the activity of an oncokinase fusion polypeptide of the invention. The process comprises admixing a pharmaceutically acceptable carrier with an agent wherein the agent is identified by a screening method comprising (1) contacting an oncokinase fusion polypeptide of the invention with a test agent, and determining the effect, if any, of the test agent on the activity of the fusion polypeptide; or (2) contacting a coding sequence for a fusion polypeptide of the invention with a test agent, and determining the effect, if any, of the test agent on the expression of the fusion polypeptide from the coding sequence.

Where the agent is a polypeptide, polynucleotide, analog or mimetic thereof, e.g. an antisense molecule, it may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA, then bombarded into skin cells. For nucleic acid therapeutic agents, a number of different delivery vehicles find use, including viral and non-viral vector systems, as are known in the art.

Those of skill in the art will readily appreciate that dose levels can vary as a function of the specific compound, the nature of the delivery vehicle, and the like. Preferred dosages for a given compound are readily determinable by those of skill in the art by a variety of means.

The subject methods find use in the treatment of a variety of different conditions in which the modulation of the subject oncokinase fusion protein activity in the host is desired. By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Methods for inhibiting fusion protein activity according to the subject invention find use in, among other applications, the treatment of cellular proliferative disease conditions, including neoplastic disease conditions, i.e., cancers. In such applications, an effective amount of an active agent, e.g., an agent that inhibits fusion protein activity, is administered to the subject in need thereof. Treatment is used broadly as defined above, e.g., to include at least an amelioration in one or more of the symptoms of the disease, as well as a complete cessation thereof, as well as a reversal and/or complete removal of the disease condition, e.g., cure.

There are many disorders associated with a dysregulation of cellular proliferation, i.e., cellular hyperproliferative disorders. The conditions of interest include, but are not limited to, the following conditions.

The subject methods may be employed in the treatment of a variety of conditions where there is proliferation and/or migration of smooth muscle cells, and/or inflammatory cells into the intimal layer of a vessel, resulting in restricted blood flow through that vessel, i.e. neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Diseases where there is hyperproliferation and tissue remodelling or repair of reproductive tissue, e.g. uterine, testicular and ovarian carcinomas, endometriosis, squamous and glandular epithelial carcinomas of the cervix, etc. are reduced in cell number by administration of the subject compounds Tumors of interest for treatment include carcinomas, e.g. colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies, e.g. neuroblastoma, gliomas, etc.; hematological malignancies, e.g. childhood acute leukemia, acute myelogenous leukemias, non-Hodgkin's lymphomas, chronic lymphocytic leukemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Some cancers of particular interest include breast cancers, which are primarily adenocarcinoma subtypes. Ductal carcinoma in situ (DCIS) is the most common type of noninvasive breast cancer. In DCIS, the malignant cells have not metastasized through the walls of the ducts into the fatty tissue of the breast. Infiltrating (or invasive) ductal carcinoma (IDC) has metastasized through the wall of the duct and invaded the fatty tissue of the breast. Infiltrating (or invasive) lobular carcinoma (ILC) is similar to IDC, in that it has the potential to metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematogenous routes to distant sites. Any organ may be involved by metastases, but lungs and liver are common sites.

Other hyperproliferative diseases of interest relate to epidermal hyperproliferation, tissue remodelling and repair. For example, the chronic skin inflammation of psoriasis is associated with hyperplastic epidermal keratinocytes as well as infiltrating mononuclear cells, including CD4+ memory T cells, neutrophils and macrophages.

The proliferation of immune cells is associated with a number of autoimmune and lymphoproliferative disorders. Diseases of interest include multiple sclerosis, rheumatoid arthritis and insulin dependent diabetes mellitus. Evidence suggests that abnormalities in apoptosis play a part in the pathogenesis of systemic lupus erythematosus (SLE). Other lymphoproliferative conditions include the inherited disorder of lymphocyte apoptosis, which is an autoimmune lymphoproliferative syndrome, as well as a number of leukemias and lymphomas. Symptoms of allergies to environmental and food agents, as well as inflammatory bowel disease, may also be alleviated by the compounds of the invention.

One hyperproliferative disorder of particular interest is hypereosinophilic disorders, e.g., hypereosinophilia syndrome or HES. Patients with hypereosinophilic syndrome (HES) present with persistent high eosinophilic cell counts. In the course of the disease acute myeloid eosinophilic leukemia often develops. The underlying cause for HES is not known. The disease is highly lethal because of significant end-organ damage. For a review of this particular disease of interest, see Bain et al., Curr. Opin. Hematol. (2000) 7:21–25.

Other disorders of particular interest are systemic mast cell disease (SMCD) (see e.g., Pardanani et al., Blood (Jul. 3, 2003) [Epub ahead of print]; and acute myeloid leukemia (AML) of the M4E0 subclass.

Also provided by the subject methods are pharmacogenomic therapeutic methods. In these pharmacogenomic applications or methods, a subject/host/patient is first diagnosed for the presence or absence of the subject fusion proteins or coding sequences therefore, e.g., using a diagnostic protocol such as those diagnostic protocols described above. The subject is then treated using a pharmacological protocol, where the suitability of the protocol for a particular subject/patient is determined using the results of the diagnosis step. As such, the subject invention provides methods of rational therapeutic protocol determination.

For example, where the diagnosis results in the determination that the host suffers from a disease condition characterized by the presence of the subject fusion proteins, an appropriate pharmacological treatment protocol, e.g., a protocol employing imatinib mesylate is then employed to treat the patient. Alternatively, where a patient is diagnosed as not having the subject fusion protein, or the patient is diagnosed as having the fusion protein but also include a variant of the fusion protein that is associated with resistance to a particular active agent (e.g., the T674I mutation) other protocols are then employed.

Additional Utilities

The subject polypeptide and nucleic acid compositions find use in a variety of additional applications. Applications in which the subject polypeptide and nucleic acid compositions find use include: (a) the identification of homologs; (b) the identification of expression regulatory factors; (c) as probes and primers in hybridization applications, e.g. PCR; (d) the identification of expression patterns in biological specimens; etc.

A. Identification of Homologs

Homologs are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Nucleic acids having a region of substantial identity to the provided sequences, e.g. allelic variants, genetically altered versions of the gene, etc., bind to the provided sequences under stringent hybridization conditions. By using probes, particularly labeled probes of DNA sequences, one can isolate homologous or related genes.

B. Identification of Expression Regulatory Factors

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995), *Mol. Med.* 1:194–205; Mortlock et al. (1996), *Genome Res.* 6:327–33; and Joulin and Richard-Foy (1995), *Eur. J. Biochem.* 232: 620–626.

The regulatory sequences may be used to identify cis acting sequences required for transcriptional or translational regulation of gene expression, especially in different tissues or stages of development, and to identify cis acting sequences and trans-acting factors that regulate or mediate gene expression. Such transcription or translational control regions may be operably linked to a fusion protein gene in order to promote expression of wild type or altered or other proteins of interest in cultured cells, or in embryonic, fet al or adult tissues, and for gene therapy.

C. Probes and Primers

Small DNA fragments are useful as primers for PCR, hybridization screening probes, etc. Larger DNA fragments, i.e. greater than 100 nt are useful for production of the encoded polypeptide, as described in the previous section. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime extension towards each other.

D. Identification of Expression Patterns in Biological Specimens

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of gene expression in the sample.

E. Preparation of Mutants

The sequence of a gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two or more, e.g., 5, 10, 20 or more nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993), *Biotechniques* 14:22; Barany (1985), *Gene* 37:111–23; Colicelli et al. (1985), *mol. Gen. Genet*. 199:537–9; and Prentki et al. (1984), *Gene* 29:303–13. Methods for site specific mutagenesis can be found in Sambrook et al., *Molecular Cloning: A Laboratory Manual*, CSH Press 1989, pp. 15.3–15.108; Weiner et al. (1993), *Gene* 126:3541; Sayers et al. (1992), *Biotechniques* 13:592–6; Jones and Winistorfer (1992), *Biotechniques* 12:528–30; Barton et al. (1990), *Nucleic Acids Res* 18:7349–55; Marotti and Tomich (1989), *Gene Anal. Tech*. 6:67–70; and Zhu (1989), *Anal Biochem* 177:120–4. Such mutated genes may be used to study structure-function relationships, or to alter properties of the protein that affect its function or regulation.

The following examples are offered by way of illustration and not by way of limitation.

EXAMPLES

Materials and Methods

A. Compounds

Imatinib mesylate was extracted from capsules of Gleevec®. Vatalanib was prepared according to the published procedure (Bold et al., J. Med. Chem. (2000) 43:2310–2323. THRX-165724 was prepared by coupling piperazine to the carboxyl group of SU6668 (Sun et al., J. Med. Chem. (1999) 42:5120–5130) as described in Example 1a of U.S. patent application Ser. No. 10/327,385.

B. cDNA Cloning, Plasmids and Oligos

Total RNA was isolated from $5\times10^7$ EOL-1 cells using the RNeasy kit (Qiagen). 100 ng of total RNA was used to make cDNA in a volume of 20 μl with a reverse oligonucleotide that primes in the 3' untranslated region of PDGFRα (5'-tccgcattgcaataaagtgg-3' (SEQ ID NO:13 (from base 3478–3459; accession no. M22734)) and the Thermoscript RT-PCR System (Gibco-BRL). 2 μl of the cDNA solution served as template in a 100 μL PCR reaction to amplify full-length NM_030917-PDGFRα (forward oligo: 5'-gttgcgctcggggcggccat-3' (SEQ ID NO:14)(from base 150–169; accession no. NM_030917), reverse oligo: 5'-ttctgaacgggatccagagg-3' (SEQ ID NO:15)(from base 3456-3437; accession no. M22734)). The PCR fragment was isolated by agarose gel electrophoresis, cloned into the TOPO-PCR vector (Invitrogen) and sequenced. The error-free sequence of a splice variant lacking the two observed alternatively spliced exons was cloned into the mammalian expression vector pcDNA 3.1(+) (Invitrogen). Patient cDNA was generated as described above, using random hexamers or the specific PDGFRα primers 5'-ggatgtcggaatatttagaa-3' (SEQ ID NO:16) and 5'-gcagaaaggtactgcctttc-3' (SEQ ID NO:17). To analyze patient cDNA for NM_030917-PDGFRα fusion transcripts the following primer pair was used: NM_030917 forward: 5'-aattatgggtttaatgaag-3' (SEQ ID NO:18)(from base 651–699; accession no. NM_030917), PDGFRα reverse: 5'-aactttcatgacaggttgg-3' (SEQ ID NO:19)(from base 2000–1982; accession no. M22734). For the PCR analysis of the genomic fusion point in EOL-1 as well as the two patients, an oligonucleotide priming 3' of PDGFRα exon 12 in the reverse orientation was combined with specific forward primers: PDGFRα genomic reverse: 5'-ttcttactaagcacaagctcagatc-3' (SEQ ID NO:20)(from base 13912–13888; accession no. AC098587); EOL-1 and patient 3 genomic forward: 5'-aagcatctaattaggtgaaactg-3' (SEQ ID NO:20)(from base 48554–48576; accession no. NT_022853). Patient 1 genomic forward: 5'-cagggaagaactggaaactc-3' (SEQ ID NO:22)(from base 22466–22485; accession no. NT_022853).

C. Cells and Cell Lines

The EOL-1 and the BaF3 cell lines were obtained from the DSMZ (Braunschweig, Germany). The basic culture medium for the EOL-1 and BaF3 cell lines was RPMI1640 (Gibco-BRL) supplemented with 10% FBS, 100 U/ml penicillin and 100 U/ml streptomycin. The medium for BaF3 cells was also supplemented with 1 ng/ml IL-3 (Biosource International). A BaF3 cell line expressing NM_030917-PDGFRα was created by electroporation of BaF3 cells at 300 mV/960 μF. After electroporation, the BaF3 cells were maintained in IL-3 containing medium for 48 h, selected in IL-3 containing medium plus 1 mg/ml G418 for 10 days, and subcloned by limiting dilution.

D. Cell Viability Assays

Cell viability was assessed by tetrazolium salt reduction using the MTT assay (Roche). In a 96-well plate, $5\times10^4$ cells/well were plated in the presence of serial dilutions of compounds. The cells were incubated for 72 h prior to addition of MTT substrate.

E. Immunoprecipitation and Western Blotting

Antibodies against PDGFRα/β and against phosphotyrosine (4G10) were purchased from Upstate Biotechnology. For each immunoprecipitation, $1\times10^7$ cells were lysed in 0.75 ml modified RIPA buffer (50 mM Tris-HCl pH 7.4, 1% NP-40, 150 mM NaCl, 1 mM EDTA, 1 mM $Na_3VO_4$, Protease inhibitor cocktail (Roche)). The lysates were incubated with the appropriate antibody and Protein G beads (Sigma) overnight at 4° C. The immunocomplexes were recovered by centrifugation, washed with RIPA buffer, boiled in sample buffer and resolved by SDS-PAGE. The proteins were transferred to a PVDF membrane (Invitrogen), blocked with PBS/0.1% Tween/3% BSA and probed with a specific antibody for 3 h at room temperature. Subsequently, the blots were washed with PBS/0.1% Tween. Specific antibody binding was detected with a horseradish-peroxidase coupled secondary antibody followed by enhanced chemiluminescence ECL (Amersham) and exposure to film. The primary antibody was typically stripped with ImmunoPure IgG Elution Buffer (Pierce) for re-probing of the blot with a second antibody.

F. Phosphorylation Inhibition Assay

Cells ($1\times10^7$) were incubated in 3 ml media with the indicated concentration of drug for 1 h. The cells were subsequently lysed and immunoprecipitated with the appropriate antibody. Then, SDS-PAGE was performed followed by immunoblotting with the anti-phosphotyrosine antibody 4G10.

G. Protein Digestion and Peptide Analysis

This work was performed by Proteomic Research Services, Inc. (PRS, Ann Arbor, Mich.). The sample was provided to PRS in the form of 50 μl of protein G immunoaffinity resin to which was bound tyrosine phosphoproteins from $1\times10^8$ EOL-1 cells via antibody 4G10. The proteins were fractionated by SDS-PAGE and visualized by staining with SYPRO ruby. Plugs were chosen for excision based on an overlay of the SYPRO-stained lane with that of a companion lane visualized by Western blotting with 4G10. The plugs were subjected to in-gel digestion with trypsin (ProGest) and a portion of the supernatant was used for analysis by matrix-assisted laser desorption-ionization mass spectrometry (MALDI/MS). MALDI/MS data were acquired on an Applied Biosystems Voyager DE-STR instrument and the observed m/z values were submitted to a search for peptide mass fingerprints by the software package ProFound from Proteometrics, querying the NCBInr database. In cases where MALDI/MS analysis was inconclusive, samples were analyzed by nano liquid chromatography followed by 2-dimensional mass spectrometry (LC/MS/MS) on a Micromass Q-Tof2 instrument. The MS/MS data were searched using the search engine Mascot from Matrix Science (www.matrixscience.com).

Example 1

Discovery of a Novel Oncokinase in Hypereosinophilic Syndrome

Imatinib mesylate (STI-571/Novartis or Gleevec™) (hereinafter "imatinib") was tested against various CML and AML cell lines. Suprisingly, it was discovered that imatinib was a potent inducer of apoptosis in EOL-1 cells. The EOL-1 cell line was established in 1984 from the peripheral blood of a 33-year-old man with acute myeloid (eosinophilic) leukemia following hypereosinophilic syndrome. The above discovery was subsequently confirmed by a report that four HES patients responded well to imatinib therapy. See Schaller et al., Med. Gen. Med. (Sep. 7, 2001) 3:9; and Lancet (May 4, 2002); 359(9317):1577–8.

In a 96-well plate, MV4–11, BV173 and EOL-1 cells were incubated with increasing concentrations of imatinib for 72 hours. Then, using the MTT assay, the viability of the cells was assessed. The absorbance at 550 nM is a measure for viability. The results are provided graphically in FIG. 1.

As can be seen in FIG. 1, imatinib potently modulates the viability of EOL-1 cells ($IC_{50}$: ~100 pM). Specifically, imatinib is a very potent inhibitor of eosinophilic cell line EOL-1. The CML cell line BV173 also shows reduced viability in the presence of imatinib but the drug is considerably less potent against this cell line ($IC_{50}$: 250 nM). Even at 10 μM, imatinib has very little effect on the viability of MV4–11 cells. The MV4–11 cell line is an acute myeloid (myelomonocytic) leukemia cell line.

Imatinib was expected to reduce the viability of the CML cell line BV173 since these cells express Bcr-Abl. MV4–11 cells do not express Bcr-Abl and as a result they are not sensitive to the drug. The high sensitivity of EOL-1 cells towards imatinib was surprising and unexpected. Like cells from most HES patients, EOL-1 cells are known to have no chromosomal translocations. Hence, the sensitivity of these cells towards imatinib cannot be based on the inhibition of Bcr-Abl. Furthermore, imatinib is more than 100-fold more potent against EOL-1 than against BV173. Other CML cell lines were tested against imatinib and all of them showed $IC_{50}$s similar to the one obtained for BV173. The lack of the typical CML chromosomal translocation and the extraordinary sensitivity of EOL-1 towards imatinib indicated that imatinib was inhibiting one or more novel targets in these cells.

In order to identify the novel imatinib target in EOL-1, the phosphoprotein profile in EOL-1 cells was first observed. EOL-1 cells were left untreated or were treated with increasing concentrations of imatinib for 2 hours. The cells were subsequently lysed and immunoprecipitated with an antibody against phosphotyrosine (4G10, obtained from Upstate Biotechnology). Subsequently, a Western Blot analysis was performed using the same anti-phosphotyrosine antibody.

The results demonstrated that, in EOL-1, there is a prominent phosphoprotein of 110 kDa molecular weight. This 110 kDa phosphoprotein is not phosphorylated in the presence of imatinib (at about 100 nM).

The 110 kDa phosphoprotein was predicted to be an activated kinase that is inhibited by imatinib. To further characterize the protein, a slice containing the 110 kDa molecular weight region was cut from a gel containing immunoprecipitated EOL-1 phosphoproteins. The proteins in the gel slice were digested with the protease trypsin and the identities of the tryptic peptide fragments were determined using mass spectroscopy. Three proteins were identified:

1. Nucleolin. Nucleolin is an abundant, 105 kDa phosphoprotein involved in the assembly of ribosomes. Based on these known features, Nucleolin was determined not to be the likely target for imatinib.
2. NM_030917 gene product. This gene is expressed in many tissues but its function is not known. However, it is not a kinase and therefore is unlikely to be a direct target for imatinib. All the NM_030917 gene product peptides mapped to the N-terminus of the protein.
3. PDGFRα. PDGFRα is a receptor tyrosine kinase. Imatinib is known to inhibit the closely related PDGFRβ with an $IC_{50}$ of 300–1000 nM. Therefore, PDGFRα was identified as a potential candidate for the imatinib target in EOL-1. Surprisingly, all the PDGFRα peptides identified mapped into the C-terminus of the protein. The C-terminus contains the kinase domain of the receptor.

Accordingly, the following experiment was performed to verify that the 110 kDa phosphoprotein contains the C-terminus of the PDGFRα receptor.

EOL-1 cells were left untreated or were treated with increasing concentrations of imatinib for 2 hours. The cells were lysed and the lysates were immunoprecipitated with an anti-PDGFRα antibody that recognizes an epitope in the C-terminus of the receptor. Subsequently, a Western Blot analysis was performed using the anti-phosphotyrosine antibody.

It was found that the anti-phosphotyrosine antibody immunoprecipitated a phosphoprotein of 110 kDa. This phosphoprotein was dephosphorylated in the presence of imatinib. The $IC_{50}$ was ~30 nM. This data suggested that the 110 kDa phosphoprotein in EOL-1 contains the C-terminus of PDGFRα.

PDGFRα is a receptor with a molecular weight of 185 kDa in its wild-type form. The fact that the C-terminus of PDGFRα was clearly present in the 110 kDa phosphoprotein meant that the receptor was mutated. Such a mutation could also explain why the kinase domain of the receptor was constitutively activated. Activated tyrosine kinases play a role in many cancers. Often, the activation is a result of a mutation in the kinase. There are two principal sets of mechanisms by which tyrosine kinases are found to be activated by mutation. The first mechanisms include point mutations, deletions or small duplications in the gene encoding the kinase. The second mechanisms include the formation of fusion proteins like Bcr-Abl which are usually a result of chromosomal translocation.

The above findings supported a conclusion that there was a fusion between the PDGFRα kinase domain and a second protein, analogous to Bcr-Abl. It is known that there are no gross chromosomal abnormalities in EOL-1 cells. There is a small deletion on chromosome 9 but the PDGFRα resides on chromosome 4. If PDGFRα was fused to another gene, that gene had to be nearby on chromosome 4 in order not to be cytogenetically obvious. NM_030917, the gene product of which was found to be present in the same gel slice as PDGFRα, is located in close proximity to the PDGFRα gene on chromosome 4. Thus, a small rearrangement on chromosome 4 would lead to the fusion of these two genes.

To test this possibility, RNA from EOL-1 cells was isolated and used to generate cDNA with a primer that primes in the non-coding, 3' region of the PDGFRα gene. The cDNA was used as a template for a PCR reaction with a primer pair priming at the very 3' end of the PDGFRα and at the very 5' end of NM_030917. The PCR yielded a fragment of about 2.5 kb that was cloned. Sequencing of various clones revealed the following:

1. NM_030917 and PDGFRα form a fusion transcript in which the intracellular domain of PDGFRα containing the kinase domain is fused to the N-terminus of NM_030917.
2. The fusion is in frame giving rise to an open reading sequence comprising 2502 base pairs corresponding to 834 amino acids.
3. The NM_030917 fragment is alternatively spliced resulting in the optional addition of one or two exons.
4. A tryptic peptide encompassing amino acid sequence from the predicted NM_030917 and PDGFRα fusion point was identified in the EOL-1 110 kDa phosphoprotein gel slice. Hence, the fusion protein is expressed in EOL-1 cells.

The coding sequence for the NM_030917-PDGFRα fusion gene is as follows:

```
ATGTCGGCCGGCGAGGTCGAGCGCCTAGTGTCGGAGCTGAGCGGCGGGACC    (SEQ ID NO:05)

GGAGGGGATGAGGAGGAAGAGTGGCTCTATGGCGGCCCATGGGACGTGCATG

TGCACAGTGATTTGGCAAAGGACCTAGATGAAAATGAAGTTGAAAGGCCAGAAG

AAGAAAATGCCAGTGCTAATCCTCCATCTGGAATTGAAGATGAAACTGCTGAAA

ATGGTGTACCAAAACCGAAAGTGACTGAGACCGAAGATGATAGTGATAGTGACA

GCGATGATGATGAAGATGATGTTCATGTCACTATAGGAGACATTAAAACGGGAG

CACCACAGTATGGGAGTTATGGTACAGCACCTGTAAATCTTAACATCAAGACAG

GGGGAAGAGTTTATGGAACTACAGGGACAAAAGTCAAAGGAGTAGACCTTGAT

GCACCTGGAAGCATTAATGGAGTTCCACTCTTAGAGGTAGATTTGGATTCTTTT

GAAGATAAACCATGGCGTAAACCTGGTGCTGATCTTTCTGATTATTTTAATTATG

GGTTTAATGAAGATACCTGGAAAGCTTACTGTGAAAAACAAAAGAGGATACGAA
```

-continued

TGGGACTTGAAGTTATACCAGTAACCTCTACTACAAATAAAATTACGGCCGAAG

ACTGTACTATGGAAGTTACACCAGGTGCAGAGATCCAAGATGGCAGATTCAATC

TTTTTAAGGTACAGCAGGGAAGAACTGGAAACTCAGAGAAAGAAACTGCCCTTC

CATCTACAAAAGCTGAGTTTACTTCTCCTCCTTCTTTGTTCAAGACTGGGCTTCC

ACCGAGCAGAAACAGCACUCTTCTCAGTCTCAGACAAGTACTGCCTCCAGAAA

AGCCTCAAGCGTTGGGAAGTGGCAGGATCGATATGGGAGGGCCGAATCAC

CTGATCTAAGGAGATTACCTGGGGCAATTGATGTTATCGGTCAGACTATAACTA

TCAGCCGAGTAGAAGGCAGGCGACGGGCAAATGAGAACAGCAACATACAGGA

CTCAAGATGGGAGTttCCAAGAGATGGACTAGTGCTTGGTCGGGTCTTGGGGT

CTGGAGCGTTTGGGAAGGTGGTTGAAGGAACAGCCTATGGATTAAGCCGGTCC

CAACCTGTCATGAAAGTTGCAGTGAAGATGCTAAAACCCACGGCCAGATCCAGT

GAAAAACAAGCTCTCATGTCTGAACTGAAGATAATGACTCACCTGGGGCCACAT

TTGAACATTGTAAACTTGCTGGGAGCCTGCACCAAGTCAGGCCCCATTTACATC

ATCACAGAGTATTGCTTCTATGGAGATTTGGTCAACTATTTGCATAAGAATAGGG

ATAGCTTCCTGAGCCACCACCCAGAGAAGCCAAAGAAAGAGCTGGATATCTTTG

GATTGAACCCTGCTGATGAAAGCACACGGAGCTATGTTATTTTATCTTTTGAAAA

CAATGGTGACTACATGGACATGAAGCAGGCTGATACTACACAGTATGTCCCCAT

GCTAGAAAGGAAAGAGGTTTCTAAATATTCCGACATCCAGAGATCACTCTATGA

TCGTCCAGCCTCATATAAGAAGAAATCTATGTTAGACTCAGAAGTCAAAAACCTC

CTTTCAGATGATAACTCAGAAGGCCTTACTTTATTGGATTTGTTGAGCTTCACCT

ATCAAGTTGCCCGAGGAATGGAGTTTTTGGCTTCAAAAAATTGTGTCCACCGTG

ATCTGGCTGCTCGCAACGTTCTCCTGGCACAAGGAAAAATTGTGAAGATCTGTG

ACTTTGGCCTGGCCAGAGACATCATGCATGATTCGAACTATGTGTCGAAAGGCA

GTACCTTTCTGCCCGTGAAGTGGATGGCTCCTGAGAGCATCTTTGACAACGTCT

ACACCACACTGAGTGATGTCTGGTCTTATGGCATTCTGCTCTGGGAGATCTTTT

CCCTTGGTGGCACCCCTTACCCCGGCATGATGGTGGATTCTACTTTCTACAATA

AGATCAAGAGTGGGTACCGGATGGCCAAGCCTGACCACGCTACCAGTGAAGTC

TACGAGATCATGGTGAAATGCTGGAACAGTGAGCCGGAGAAGAGACCCTCCTT

TTACCACCTGAGTGAGATTGTGGAGAATCTGCTGCCTGGACAATATAAAAAGAG

TTATGAAAAAATTCACCTGGACTTCCTGAAGAGTGACCATCCTGCTGTGGCACG

CATGCGTGTGGACTCAGACAATGCATACATTGGTGTCACCTACAAAAACGAGGA

AGACAAGCTGAAGGACTGGGAGGGTGGTCTGGATGAGCAGAGACTGAGCGCT

GACAGTGGCTACATCATTCCTCTGCCTGACATTGACCCTGTCCCTGAGGAGGA

GGACCTGGGCAAGAGGAACAGACACAGCTCGCAGACCTCTGAAGAGAGTGCC

ATTGAGACGGGTTCCAGCAGTTCCACCTTCATCAAGAGAGAGGACGAGACCAT

TGAAGACATCGACATGATGGACGACATCGGCATAGACTCTTCAGACCTGGTGG

AAGACAGCTTCCTGTAA

The underlined sequences are alternatively spliced. None or one or both sequences may be present in a given transcript. These additional alternatives are provided as SEQ ID NOS: 06, 07 and 08 in the attached Sequence Listing.

The above coding sequence encodes a NM_030917-PDGFRα fusion protein product having the following amino acid sequence:

```
MSAGEVERLVSELSGGTGGDEEEEWLYGGPWDVHVHSDLAKDLDENEVERPEEE   (SEQ ID NO:01)

NASANPPSGIEDETAENGVPKPKVTETEDDSDSDSDDDEDDVHVTIGDIKTGAPQY

GSYGTAPVNLNIKTGGRWGTTGTKVKGVDLDAPGSINGVPLLEVDLDSFEDKPWR

KPGADLSDYFNYGFNEDTWKAYCEKQKRIRMGLEVIPVTSTTNKITAEDCTMEVTP

GAEIQDGRFNLFKVQQGRTGNSEKETALPSTKAEFTSPPSLFKTGLPPSRNSTSSQ

SQTSTASRKANSSVGKWQDRYGRAESPDLRRLPGAIDVIGQTITISRVEGRRRANE

NSNIQLPYDSRWEFPRDGLVLGRVLGSGAFGKWEGTAYGLSRSQPVMKVAVKML

KPTARSSEKQALMSELKIMTHLG-
PHLNIVNLLGACTKSGPIYIITEYCFYGDLVNYLH

KNRDSFLSHHPEKPKKELDIFGLNPADESTRSYVILSFENNGDYMDMKQADTTQYV

PMLERKEVSKYSDIQRSLY-
DRPASYKKKSMLDSEVKNLLSDDNSEGLTLLDLLSFTY

QVARGMEFLASKNCVHRDLAARNVLLAQGKIVKICDFGLARDIMHDSNYVSKGSTF

LPVKWMAPESIFDNLYTTLSDVWSY-
GILLWEIFSLGGTPYPGMMVDSTFYNKIKSGY

RMAKPDHATSEVYEIMVKCWNSEPE-
KRPSFYHLSEIVENLLPGQYKKSYEKIHLDFL

KSDHPAVARMRVDSDNAYIGVTYKNEEDKLKDWEGGLDEQRLSADSGYIIPLPDID

PVPEEEDLGKRNRHSSQTSEESAI-
ETGSSSSTFIKREDETIEDIDMMDDIGIDSSDLV

EDSFL*
```

The underlined peptides are alternatively spliced sequences. None or one or both sequences may be present in a given fusion protein. These alternative sequences are provided as SEQ ID NOS: 02, 03 and 04 in the attached sequence listing.

Double Underline: Peptide identified by mass spec which contains sequences from NM_030917 and PDGFRα. (The fusion is between Q (NM_030917) and L (PDGFRα)

Primer pairs flanking the fused exons of NM_030917 and PDGFRα on the normal chromosome 4 were designed. Using genomic DNA, those exons in EOL-1 cells as well as other leukemia cell lines were amplified using the designed primer pairs in a PCR protocol. When the 5' primer of the fused NM_030917 exon was combined with the 3' primer of the fused PDGFRα exon, a fragment of 1100 base pairs from EOL-1 genomic DNA but not from any other cell line tested was obtained in the PCR protocol. This fragment contained the genomic recombination point and it is derived from the mutant chromosome 4. The 1100 base pair fragment was sequenced to characterize the genomic recombination point. The following observations were made:

1. The recombination point deletes approximately one million base pairs on chromosome 4. This leads to the fusion of an intron in NM_030917 to the middle of exon 12 in PDGFRα.
2. The splice donor dinucleotide GT in the NM_030917 intron recognizes the first AG dinucleotide in the PDGFR alpha exon as the splice acceptor site. The splicing reaction results in a fusion that maintains the reading frame of the PDGFR gene.

Deletion of 1 Megabase fuses NM_030917 and exon 12 of PDGFRα on chromosome 4:

```
GGAGATTACCTGGGGCAATT                                  (SEQ ID NO:09)

GATGTTATCGGTCAGACTAT GTTTAGTATT

TTAAAATAAATAATTTTCTTTAACTGAAGGATGATATCAACATTATAATTTAATTTA

TTCAATAGATAGTCATAGTGCTATGCTGTGTTTTAGGTGATACAAAGAGATTTAA

AATGTGAAGCCAGTCATTTATTATAAAGGCATTTCCAGTTAGAATTTATAATCTCT

GAATCTTTTTTTTAATAGGGTTTTCTTTCTTTTCCTTGGTAGAAACATAGTACAGGT

TGAGTATCTCTTATCTGAAATGCTTGGGACCAGAAGTGTATCAGATTTTGAAATG
```

-continued

```
TTTGGATTTTGAAATGTTCATACGTATGTAATCTTAGAGATGAGACCCAAGTCTA

AACATGAAATTTATGTTTCATAAATAAGTTATTTAATTTGTTATAATGATTTGTTAA

TTTATGATAATCTTTTTTCCTTTGGCAACCCTGAGTAAACTGTGTAGTGGGCCTG

AGTTTTGATTGTGATCCGTCACATGTGAGGTTGGGTGTGGAATTTTCCACTTGT

GATAAAATGTTGATGCTCAAAATGTTTCGGATTTTAGAGCATTTCAGATTTCAGA

TTTTTGGATTAGGAATACTCAACTTGTATATAGGTTTACTGAATGAAAAATAAAAC

ACCACCAGTGATTTTACCACCTAAAGATAACCACATCTGGTACATCTCTTGATAC

TAAGCAAAATTGGGATACTATTATAATTATATTTCTGTGTATACTTTTTCCCCAT

CTAAAATTATCATTTGTATGTTTTCATATTCTTAAAATATGATTAAAATATCTTCAT

GATAGCTTCATTGGATAAATATACCATGATTTATFUAATGTGACATTTCTGGAGG

TGGCGTAGAGCTGCTTTGTTTTTAGGTGAAAAATTGAGGGGAGATAAATTATCA

GTAAGTTGGATAATTAATAATTAGAACTTTAATAACTGAGACTTCCAGCTATTCATT

TTGGCCATACTTTTTTTCATTATTTATTCC

. . .
about 1 Megabase
. . .

TGGTTTGAGAGATGGTACTGCCTATCCCTAAAATGAACCAGGCAGCCCTCACAC     (SEQ ID NO:10)

TTCCCCACCAGCAGTGAGAGATTCCTGGCTCAGACACAGCCACACTACCTTGCT

GCCCCTGTGCATGTCTGCCAGGAAACTTTTCATTGTGCCTCTCTCTCTTGTCAC

GTAGCCCTGCGTTCTGAACTCACGGTGGCTGCTGCAGTCCTGGTGCTGTTGGT

GATTGTGATCATCTCACTTATTGTCCTGGTTGTCATTTGGAAACAGGTAGATAT

TTTCTCATAAAACTAAAGATCTTTGAAGCCAATGAGAACAAGCATAGCAACCTAG

TTCAGTGCTTGGCACAGAGAAGGAGCTCAGCAATTACATGTGGAGTGAACGTT

GTTGGACTCTACTGTGTCCAGTCACTGTGCTGCTTCAGTGAAGCTCTGGTGCAC

TGGGACTTTGGTAATTCACCAGTTACCTGTCCTGGTCATTTATAGAAACCGAGG

TATGAAATTCGCTGGAGGGTCATTGAATCAATCAGCCCAGATGGACATGAATA

TATTTATGTGGACCCGAACTATCAGCCGA

GTAGAAGGCAGGCGACGGGCGTAAGTTCCATGGGGTAACCTCCCAAGACTCCCTT

TTCCCTTGCACACAACTTTACAATTTATAGGCCTTGGCAGAATAGAGATCTGAGC

TGTGCTTAGTAAGAACTAGGCAATGGAAATTTGCTTTCAGAAATACATTTCTGT

CTTGACAGTAAGTTAA
Non bold: intron
Bold: exon
```

italic bases denote the contiguous sequence after the 1 megabase deletion has occured.

ATACAGGTTTAG . . . GACCCGATGCAGCTGCCT (SEQ ID NO:11 and 12)

The underlined bases denote the splice donor and splice acceptor sites of the intron that comprise the fusion point.

In summary, eosinophilia cells in patients have been shown to undergo apoptosis when exposed to imatinib. The eosinophilic AML cell line EOL-1 has been shown above to be similarly sensitive to imatinib and therefore represents a good model system to identify targets for imatinib in this disease. The EOL-1 cells were discovered to have a chromosomal rearrangement on chromosome 4 which leads to the expression of a fusion protein consisting of an uncharacterized protein and the cytoplasmic domain of PDGFRα. The fusion protein is highly phosphorylated in EOL-1 cells which is a reflection of an activated state of the PDGFRα kinase domain. The phosphorylation of the fusion protein can be inhibited with imatinib. The $IC_{50}$ is ~30 nM. The above data show that the kinase domain of PDGFRα expressed as a fusion protein is a target for imatinib in EOL-1.

Thus, the above results show that PDGFRα fusion proteins play an important role in hypereosinophilic syndrome and acute myeloid (eosinophilic) leukemia, analogous to Bcr-Abl in CML. The fusion proteins may differ in the exact genomic location where NM_030917 and PDGFRα are recombined.

Furthermore, since fusion with NM_030917 is able to activate the kinase domain of PDGFRα, then fusion of an N-terminal domain of the NM_030917 protein activates other kinase domains in certain embodiments. For example, just downstream from PDGFRα on chromosome 4 are two more receptor tyrosine kinases, namely c-kit and VEGFR-2. As such, in other hyperproliferative diseases, fusions of NM_030917 and c-kit or VEGFR-2 are expected to be present.

Example 2

Inhibition of Cellular NM 030917-PDGFRα Autophosphorylation

Using Western Blot analysis, the potency of THRX-165724 (described in Example 1 of patent application Ser. No.10/327,385) and vatalanib (PTK787) (described in Examples 1 to 4 of U.S. Pat. No. 6,258,812 B1) in inhibiting cellular NM_030917-PDGFRα autophosphorylation was assessed. It was found that both of these kinase inhibitors have activity in this assay. In parallel, both inhibitors were tested for their ability to induce apoptosis in EOL-1 cells. The $IC_{50}$s obtained in the two assays are listed below:

| Compound | Inhibition of Autophosphorylation | Inhibition of Cell Viability |
|---|---|---|
| THRX-165724 | 10–30 nM | 10 nM |
| vatalanib (PTK787) | 100–300 nM | 100 nM |

The $IC_{50}$s for THRX-165724 and vatalanib (PTK787) correlate well between the two assays. The above results demonstrate that THRX-165724 and vatalanib (PTK787) at 10–30 and 100–300 nM, respectively, induce apoptosis by inhibiting NM_030917-PDGFRα.

Example 3

Cell-Transforming Potential of NM 030917-PDGFRα

Mutationally activated tyrosine kinases, as found in many cancers, can transform the murine myeloid cell line BaF3 to interleukin-3 independence. In order to determine if NM_030917-PDGFRα has the ability to transform cells, a BaF3 cell line was established. BaF3 cells expressing NM_030917-PDGFRα from EOL-1 were found to be IL-3 independent. The fusion protein in these cells was constitutively phosphorylated and the phosphorylation was inhibited by imatinib with an $IC_{50}$ of 30 nM, the same value as obtained in EOL-1. Inhibition with imatinib, vatalanib and THRX-165724 resulted in reduced viability of the BaF3 NM_030917-PDGFRα cells with $IC_{50}$s similar to the potency of the drugs in EOL-1. The effect of the inhibitors was overcome in the presence of IL-3. NM_030917-PDGFRα is also likely to be the target for imatinib, vatalanib and THRX-165724 in EOL-1 since the expression of the fusion gene conferred IL-3 independent growth to BaF3 cells which was inhibited by the three drugs at concentrations similar to those at which they inhibited the viability of EOL-1 cells. The viability of these BaF3 cells in the presence of the PDGFRα inhibitors could be maintained by exogenous IL-3.

Example 4

Identification of NM 030917-PDGFRα in HES Patient Cells

Figure 3A:
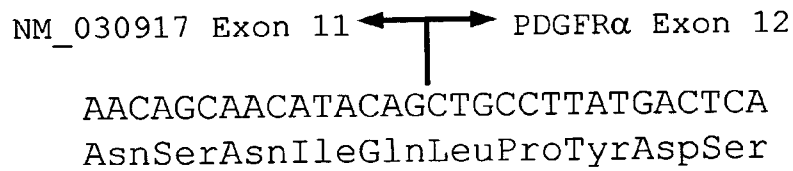
FIGS. 3A and 3B provide sequence data of fusion points found in NM_030917-PDGFRα fusion protein coding sequences found in two different EOS patients.
Figure 3A:
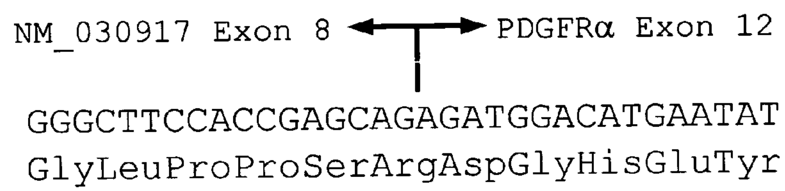
Figure 3B:
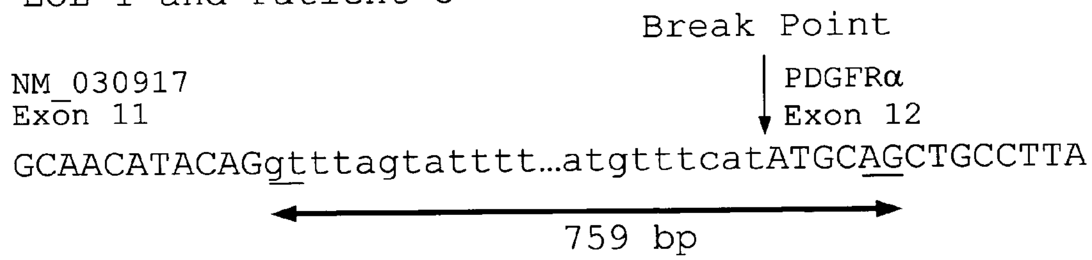
Figure 3B:
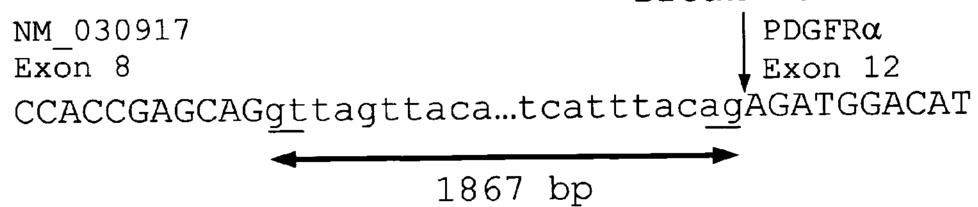

In order to determine if the NM_030917-PDGFRα fusion was present in HES patients, blood cells from four patients diagnosed with HES were obtained. Patients 1 and 2 had been treated with imatinib. Patient 1 responded to treatment, but patient 2 did not. After showing a complete hematologic remission, patient 1 relapsed and died. This patient had multiple clonal cytogenetic abnormalities which led to the diagnosis of CEL. Genomic DNA as well as total RNA and cDNA were prepared from all patient cells except for patient 1 for whom only genomic DNA, but no RNA and cDNA were obtained from cells before imatinib treatment. The cDNA samples were subjected to PCR with a primer pair spanning the fusion point determined in EOL-1 cells. In the samples from patients 1 and 3, fragments could be amplified from the cDNA that constituted in-frame fusion transcripts between NM_030917 and PDGFRα (FIG. 3A). No NM_030917-PDGFRα fusion was detected in patients 2 and 4. In patient 1, the fusion transcript connects exon 8 of NM_030917 within exon 12 of PDGFRα. A similar approach as for EOL-1 was used to identify the genomic breakpoint. In patient 1, the intronic break is at an AG dinucleotide that serves as the splice acceptor site so that exon 8 in NM_030917 and part of exon 12 in PDGFRα are fused in-frame in the fusion transcript (FIG. 3B). The NM_030917-PDGFRα fusion in patient 1 was detected in genomic DNA preparations derived from cells taken before the start of imatinib therapy and at the time of relapse. The analysis of NM_030917-PDGFRα cDNA at the time of relapse revealed a point mutation in the PDGFRα kinase domain. The mutation affects amino acid position 674 in PDGFRα resulting in the substitution of threonine by isoleucine (T674I).

In patient 3, the fusion transcript as well as the genomic break are identical to the mutation found in EOL-1 cells (FIGS. 3A and 3B).

Amplification and sequencing of genomic DNA from EOL-1 cells revealed that the genomic breakpoint junctions fell within an intron following exon 11 of NM_030917 and within exon 12 of PDGFRα. The same mutation was observed in patient 3 and a similar submicroscopic deletion was discovered in patient 1. In patient 1 the resulting transcript fused a different site in the NM_030917 gene to a distinct site in PDGFRα exon 12. Exon 12 encompasses the cytoplasmic juxtamembrane region of PDGFRα, followed by the kinase domain.

Patient 1 relapsed and died after initially having shown a complete remission in response to imatinib. At the time of relapse, this patient had a T674I mutation in the PDGFRα kinase domain. T674 in PDGFRα corresponds to T315 in c-Abl. Based on the crystal structure of the catalytic domain of c-Abl bound to a derivative of imatinib, T315 forms part of the imatinib binding pocket and establishes a hydrogen bond with the drug (Schindler et al., Science (2000) 289: 1938–1942). The T315I mutation ablates the kinase inhibitory activity of imatinib for Bcr-Abl and it is one of the most common mutations found in CML patients who are resistant to the drug (Gorre et al., Science (2001) 293:876–880; Branford et al., Blood (2002) 99:3472–3475). The above indicates that that the T674I mutation underlies the relapse of patient 1 and therefore provides further evidence that NM_030917-PDGFRα is the target of imatinib.

Two reports describe patients with myeloproliferative disorders with eosinophilia who have chromosomal translocations at 4q11–12 (Duell et al., Cancer Genet. Cytogenet. (1997) 94:91–94; Schoffski et al., Ann. Hematol. (2000) 79:95–98). These translocations may involve either NM_030917 or PDGFRα leading to different disease promoting fusion proteins. For example, NM_030917 may play a role analogous to that played by Tel or Bcr-promoting dimerization and, thus, the activation of known oncogenic fusion kinases. Like PDGFRα, the c-Kit gene is located on chromosome 4q12. Submicroscopic deletions could also result in NM_030917-c-Kit fusions. A search of the NCBI EST database reveals that NM_030917 is expressed in many tissues and organs suggesting that NM_030917-fusion kinases may not be restricted to cells of hematological origin. The protein encoded by NM_030917 is homologous (26% over 307 residues) to yeast protein FIP1, a component of a polyadenylation factor (Preker et al., Cell (1995) 81:379–389).

PDGFRα shares a high degree of homology with PDGFRβ (Matsui et al., Science (1989) 243: 800–804. PDGFRβ is a target for various chromosomal translocations in chronic myeloproliferative diseases that result in the expression of fusion kinases; e.g., Tel-PDGFRβ and Rab5-PDGFRβ (Golub et al., Cell (1994) 77:307–316; Magnusson et al., Blood (2001) 98:2518–2525; Ross et al., Blood (1998) 91:44194426; Abe et al., Blood (1997) 90:4271–4277; Kulkarni et al., Cancer Res. (2000) 60: 3592–3598; Schwaller et al., Blood (2001) 97:3910–3918. Like PDGFRβ, PDGFRα has recently been described as part of a fusion gene. Baxter et al. (Hum. Mol. Genet. (2002) 11:1391–1397) identified two atypical CML patients with a t(4;22)(q12;q11) translocation resulting in Bcr-PDGFRα fusions. Similar to the NM_030917-PDGFRα fusion we have discovered, both Bcr-PDGFRα fusions involve translocation into exon 12 of PDGFRα. Indeed, one of the two Bcr-PDGFRα fusions produces precisely the same PDGFRα fragment that we observed in NM_030917-PDGFRα from EOL-1 cells.

In summary, the above experiments demonstrate that the novel NM_030917-PDGFRα genomic rearrangement, discovered in the eosinophilic EOL-1 cell line, is present in a subset of patients diagnosed with HES. Cell viability and phosphorylation data show that the NM_030917-PDGFRα kinase encoded by the novel fusion gene plays a central role in the disease process of these HES patients. Accordingly, HES in which the NM_030917-PDGFRα fusion is detected may be described as chronic eosinophilic leukemia.

It is evident from the above results and discussion that the subject invention provides for important new targets for the treatment of various disease conditions, including proliferative diseases, such as cancer. In addition to providing the subject targets, the invention further provides important new methods of diagnosis and treatment, which will provide significant benefits the medical and related fields. Accordingly, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of determining whether a human suffers from a hyperproliferative disease condition, said method comprising:
   (a) assaying said human for the presence of a polynucleotide comprising a coding sequence for a fusion polypeptide having a constitutively activated kinase activity to obtain an assay result, wherein said fusion polypeptide is not the product of a translocation event and comprises:
      (i) a domain of a tyrosine kinase chosen from PDGFRα, c-Kit and VEGFR-2; and
      (ii) a kinase activating domain of a protein encoded by the NM$_{13}$ 030917 gene; and
   (b) employing said assay result to determine whether said mammalian host suffers from said hyperproliferative disease condition.

2. The method according to claim 1, wherein said method further comprises obtaining a sample from said host.

3. The method according to claim 2, wherein said assaying comprises screening said sample for the presence of the polynucleotide.

4. The method according to claim 2, wherein said assaying comprises screening said sample for a chromosomal deletion that produces the polynucleotide.

5. The method according to claim 1, wherein said tyrosine kinase is PDGFRα.

6. The method according to claim 1, wherein said tyrosine kinase is c-Kit.

7. The method according to claim 1, wherein said tyrosine kinase is VEGFR-2.

8. The method according to claim 1, wherein said fusion polypeptide has an amino acid sequence that is identical to or has at least 95% identity with a sequence chosen from SEQ ID NO:01, SEQ ID NO:02; SEQ ID NO:03 and SEQ ID NO:04.

9. The method according to claim 1, wherein said polynucleotide has a sequence of residues that is identical to or has at least 95% identity with a sequence chosen from SEQ ID NO:05, SEQ ID NO:06; SEQ ID NO:07 and SEQ ID NO:08 and complements thereof.

10. A method of determining whether a human suffers from a hyperproliferative disease condition, said method comprising:
   (a) assaying said human for the presence of a polynucleotide comprising a coding sequence for a fusion polypeptide having a constitutively activated kinase activity to obtain an assay result, wherein said fusion polypeptide is not the product of a translocation event and comprises:
      (i) a domain of PDGFRα; and
      (ii) a kinase activating domain of a protein encoded by the NM$_{13}$ 030917 gene; and
   (b) employing said assay result to determine whether said mammalian host suffers from said hyperproliferative disease condition.

11. The method according to claim 10, wherein said method further comprises obtaining a sample from said host.

12. The method according to claim 11, wherein said assaying comprises screening said sample for the presence of the polynucleotide.

13. The method according to claim 11, wherein said assaying comprises screening said sample for a chromosomal deletion that produces the polynucleotide.

14. The method according to claim 10, wherein said fusion polypeptide has an amino acid sequence that is identical to or has at least 95% identity with a sequence chosen from SEQ ID NO:01, SEQ ID NO:02; SEQ ID NQ:03 and SEQ ID NO:04.

15. The method according to claim 10, wherein said polynucleotide has a sequence of residues that is identical to or has at least 95% identity with a sequence chosen from SEQ ID NO;05, SEQ ID NO:06; SEQ ID NO:07 and SEQ ID NO:08 and complements thereof.

16. A method of determining whether a human suffers from a hyperproliferative disease condition, said method comprising:
   (a) assaying said human for the presence of a polynucleotide comprising a coding sequence for a fusion polypeptide having a constitutively activated kinase activity to obtain an assay result, wherein said fusion polypeptide Is not the product of a translocation event and comprises:
      (i) a domain of c-Kit; and
      (ii) a kinase activating domain of a protein encoded by the NM_030917 gene; and
   (b) employing said assay result to determine whether said mammalian host suffers from said hyperproliferative disease condition.

17. The method according to claim 16, wherein said method further comprises obtaining a sample from said host.

18. The method according to claim 17, wherein said assaying comprises screening said sample for the presence of the polynucleotide.

19. The method according to claim 17. wherein said assaying comprises screening said sample for a chromosomal deletion that produces the polynucleotide.

20. A method of determining whether a human suffers from a hyperproliferative disease condition, said method comprising:
   (a) assaying said human for the presence of a polynucleotide comprising a coding sequence for a fusion polypeptide having a constitutively activated kinase activity to obtain an assay result, wherein said fusion polypeptide is not the product of a translocation event and comprises:

(i) a domain of VEGFR-2; and (ii) a kinase activating domain of a protein encoded by the $NM_{13}$ 030917 gene; and (b) employing said assay result to determine whether said mammalian host suffers from said hyperproliferative disease condition.

21. The method according to claim 20, wherein said method further comprises obtaining a sample from said host.

22. The method according to claim 21, wherein said assaying comprises screening said sample for the presence of the polynucleotide.

23. The method according to claim 21, wherein said assaying comprises screening said sample for a chromosomal deletion that produces the polynucleotide.

* * * * *

UNITED STATES PATENT AND TRADEMARK OFFICE

CERTIFICATE OF CORRECTION

PATENT NO. : 7,195,876 B2
APPLICATION NO. : 10/637356
DATED : February 27, 2007
INVENTOR(S) : Briesewitz et al.

It is certified that error appears in the above-identified patent and that said Letters Patent is hereby corrected as shown below:

At Column 83
line 29, "$NM_{13}$ 030917" should read --NM_030917--.

At Column 83
line 67, "$NM_{13}$ 030917" should read --NM_030917--.

At Column 85
line 3, "$NM_{13}$ 030917" should read --NM_030917--.

Signed and Sealed this

Thirty-first Day of July, 2007

JON W. DUDAS
*Director of the United States Patent and Trademark Office*

UNITED STATES PATENT AND TRADEMARK OFFICE

CERTIFICATE OF CORRECTION

PATENT NO. : 7,195,876 B2
APPLICATION NO. : 10/637356
DATED : March 27, 2007
INVENTOR(S) : Briesewitz et al.

It is certified that error appears in the above-identified patent and that said Letters Patent is hereby corrected as shown below:

At Column 83
line 29, "$NM_{13}$ 030917" should read --NM_030917--.

At Column 83
line 67, "$NM_{13}$ 030917" should read --NM_030917--.

At Column 85
line 3, "$NM_{13}$ 030917" should read --NM_030917--.

This certificate supersedes Certificate of Correction issued July 31, 2007.

Signed and Sealed this

Twenty-first Day of August, 2007

JON W. DUDAS
*Director of the United States Patent and Trademark Office*

SEQUENCE LISTING

<160> NUMBER OF SEQ ID NOS: 22

<210> SEQ ID NO 1
<211> LENGTH: 849
<212> TYPE: PRT
<213> ORGANISM: homo sapiens

<400> SEQUENCE: 1

Met Ser Ala Gly Glu Val Glu Arg Leu Val Ser Glu Leu Ser Gly Gly
1               5                   10                  15

Thr Gly Gly Asp Glu Glu Glu Glu Trp Leu Tyr Gly Gly Pro Trp Asp
            20                  25                  30

Val His Val His Ser Asp Leu Ala Lys Asp Leu Asp Glu Asn Glu Val
        35                  40                  45

Glu Arg Pro Glu Glu Glu Asn Ala Ser Ala Asn Pro Pro Ser Gly Ile
    50                  55                  60

Glu Asp Glu Thr Ala Glu Asn Gly Val Pro Lys Pro Lys Val Thr Glu
65                  70                  75                  80

Thr Glu Asp Asp Ser Asp Ser Asp Ser Asp Asp Asp Glu Asp Asp Val
                85                  90                  95

His Val Thr Ile Gly Asp Ile Lys Thr Gly Ala Pro Gln Tyr Gly Ser
            100                 105                 110

-continued

```
Tyr Gly Thr Ala Pro Val Asn Leu Asn Ile Lys Thr Gly Gly Arg Val
        115                 120                 125

Tyr Gly Thr Thr Gly Thr Lys Val Lys Gly Val Asp Leu Asp Ala Pro
    130                 135                 140

Gly Ser Ile Asn Gly Val Pro Leu Leu Glu Val Asp Leu Asp Ser Phe
145                 150                 155                 160

Glu Asp Lys Pro Trp Arg Lys Pro Gly Ala Asp Leu Ser Asp Tyr Phe
                165                 170                 175

Asn Tyr Gly Phe Asn Glu Asp Thr Trp Lys Ala Tyr Cys Glu Lys Gln
            180                 185                 190

Lys Arg Ile Arg Met Gly Leu Glu Val Ile Pro Val Thr Ser Thr Thr
        195                 200                 205

Asn Lys Ile Thr Ala Glu Asp Cys Thr Met Glu Val Thr Pro Gly Ala
    210                 215                 220

Glu Ile Gln Asp Gly Arg Phe Asn Leu Phe Lys Val Gln Gln Gly Arg
225                 230                 235                 240

Thr Gly Asn Ser Glu Lys Glu Thr Ala Leu Pro Ser Thr Lys Ala Glu
                245                 250                 255

Phe Thr Ser Pro Pro Ser Leu Phe Lys Thr Gly Leu Pro Pro Ser Arg
            260                 265                 270

Asn Ser Thr Ser Ser Gln Ser Gln Thr Ser Thr Ala Ser Arg Lys Ala
        275                 280                 285

Asn Ser Ser Val Gly Lys Trp Gln Asp Arg Tyr Gly Arg Ala Glu Ser
    290                 295                 300

Pro Asp Leu Arg Arg Leu Pro Gly Ala Ile Asp Val Ile Gly Gln Thr
305                 310                 315                 320

Ile Thr Ile Ser Arg Val Glu Gly Arg Arg Arg Ala Asn Glu Asn Ser
                325                 330                 335

Asn Ile Gln Leu Pro Tyr Asp Ser Arg Trp Glu Phe Pro Arg Asp Gly
            340                 345                 350

Leu Val Leu Gly Arg Val Leu Gly Ser Gly Ala Phe Gly Lys Val Val
        355                 360                 365

Glu Gly Thr Ala Tyr Gly Leu Ser Arg Ser Gln Pro Val Met Lys Val
    370                 375                 380

Ala Val Lys Met Leu Lys Pro Thr Ala Arg Ser Ser Glu Lys Gln Ala
385                 390                 395                 400

Leu Met Ser Glu Leu Lys Ile Met Thr His Leu Gly Pro His Leu Asn
                405                 410                 415

Ile Val Asn Leu Leu Gly Ala Cys Thr Lys Ser Gly Pro Ile Tyr Ile
            420                 425                 430

Ile Thr Glu Tyr Cys Phe Tyr Gly Asp Leu Val Asn Tyr Leu His Lys
        435                 440                 445

Asn Arg Asp Ser Phe Leu Ser His His Pro Glu Lys Pro Lys Lys Glu
    450                 455                 460

Leu Asp Ile Phe Gly Leu Asn Pro Ala Asp Glu Ser Thr Arg Ser Tyr
465                 470                 475                 480

Val Ile Leu Ser Phe Glu Asn Asn Gly Asp Tyr Met Asp Met Lys Gln
                485                 490                 495

Ala Asp Thr Thr Gln Tyr Val Pro Met Leu Glu Arg Lys Glu Val Ser
            500                 505                 510

Lys Tyr Ser Asp Ile Gln Arg Ser Leu Tyr Asp Arg Pro Ala Ser Tyr
        515                 520                 525
```

-continued

```
Lys Lys Lys Ser Met Leu Asp Ser Glu Val Lys Asn Leu Leu Ser Asp
    530                 535                 540

Asp Asn Ser Glu Gly Leu Thr Leu Leu Asp Leu Leu Ser Phe Thr Tyr
545                 550                 555                 560

Gln Val Ala Arg Gly Met Glu Phe Leu Ala Ser Lys Asn Cys Val His
                565                 570                 575

Arg Asp Leu Ala Ala Arg Asn Val Leu Leu Ala Gln Gly Lys Ile Val
            580                 585                 590

Lys Ile Cys Asp Phe Gly Leu Ala Arg Asp Ile Met His Asp Ser Asn
        595                 600                 605

Tyr Val Ser Lys Gly Ser Thr Phe Leu Pro Val Lys Trp Met Ala Pro
    610                 615                 620

Glu Ser Ile Phe Asp Asn Leu Tyr Thr Thr Leu Ser Asp Val Trp Ser
625                 630                 635                 640

Tyr Gly Ile Leu Leu Trp Glu Ile Phe Ser Leu Gly Gly Thr Pro Tyr
                645                 650                 655

Pro Gly Met Met Val Asp Ser Thr Phe Tyr Asn Lys Ile Lys Ser Gly
            660                 665                 670

Tyr Arg Met Ala Lys Pro Asp His Ala Thr Ser Glu Val Tyr Glu Ile
        675                 680                 685

Met Val Lys Cys Trp Asn Ser Glu Pro Glu Lys Arg Pro Ser Phe Tyr
    690                 695                 700

His Leu Ser Glu Ile Val Glu Asn Leu Leu Pro Gly Gln Tyr Lys Lys
705                 710                 715                 720

Ser Tyr Glu Lys Ile His Leu Asp Phe Leu Lys Ser Asp His Pro Ala
                725                 730                 735

Val Ala Arg Met Arg Val Asp Ser Asp Asn Ala Tyr Ile Gly Val Thr
            740                 745                 750

Tyr Lys Asn Glu Glu Asp Lys Leu Lys Asp Trp Glu Gly Gly Leu Asp
        755                 760                 765

Glu Gln Arg Leu Ser Ala Asp Ser Gly Tyr Ile Ile Pro Leu Pro Asp
    770                 775                 780

Ile Asp Pro Val Pro Glu Glu Glu Asp Leu Gly Lys Arg Asn Arg His
785                 790                 795                 800

Ser Ser Gln Thr Ser Glu Glu Ser Ala Ile Glu Thr Gly Ser Ser Ser
                805                 810                 815

Ser Thr Phe Ile Lys Arg Glu Asp Glu Thr Ile Glu Asp Ile Asp Met
            820                 825                 830

Met Asp Asp Ile Gly Ile Asp Ser Ser Asp Leu Val Glu Asp Ser Phe
        835                 840                 845

Leu


<210> SEQ ID NO 2
<211> LENGTH: 834
<212> TYPE: PRT
<213> ORGANISM: homo sapiens

<400> SEQUENCE: 2

Met Ser Ala Gly Glu Val Glu Arg Leu Val Ser Glu Leu Ser Gly Gly
 1               5                  10                  15

Thr Gly Gly Asp Glu Glu Glu Glu Trp Leu Tyr Gly Asp Glu Asn Glu
            20                  25                  30

Val Glu Arg Pro Glu Glu Glu Asn Ala Ser Ala Asn Pro Pro Ser Gly
        35                  40                  45
```

-continued

```
Ile Glu Asp Glu Thr Ala Glu Asn Gly Val Pro Lys Pro Lys Val Thr
    50                  55                  60

Glu Thr Glu Asp Asp Ser Asp Ser Asp Ser Asp Asp Asp Glu Asp Asp
65                  70                  75                  80

Val His Val Thr Ile Gly Asp Ile Lys Thr Gly Ala Pro Gln Tyr Gly
                85                  90                  95

Ser Tyr Gly Thr Ala Pro Val Asn Leu Asn Ile Lys Thr Gly Gly Arg
            100                 105                 110

Val Tyr Gly Thr Thr Gly Thr Lys Val Lys Gly Val Asp Leu Asp Ala
        115                 120                 125

Pro Gly Ser Ile Asn Gly Val Pro Leu Leu Glu Val Asp Leu Asp Ser
    130                 135                 140

Phe Glu Asp Lys Pro Trp Arg Lys Pro Gly Ala Asp Leu Ser Asp Tyr
145                 150                 155                 160

Phe Asn Tyr Gly Phe Asn Glu Asp Thr Trp Lys Ala Tyr Cys Glu Lys
                165                 170                 175

Gln Lys Arg Ile Arg Met Gly Leu Glu Val Ile Pro Val Thr Ser Thr
            180                 185                 190

Thr Asn Lys Ile Thr Ala Glu Asp Cys Thr Met Glu Val Thr Pro Gly
        195                 200                 205

Ala Glu Ile Gln Asp Gly Arg Phe Asn Leu Phe Lys Val Gln Gln Gly
    210                 215                 220

Arg Thr Gly Asn Ser Glu Lys Glu Thr Ala Leu Pro Ser Thr Lys Ala
225                 230                 235                 240

Glu Phe Thr Ser Pro Pro Ser Leu Phe Lys Thr Gly Leu Pro Pro Ser
                245                 250                 255

Arg Asn Ser Thr Ser Ser Gln Ser Gln Thr Ser Thr Ala Ser Arg Lys
            260                 265                 270

Ala Asn Ser Ser Val Gly Lys Trp Gln Asp Arg Tyr Gly Arg Ala Glu
        275                 280                 285

Ser Pro Asp Leu Arg Arg Leu Pro Gly Ala Ile Asp Val Ile Gly Gln
    290                 295                 300

Thr Ile Thr Ile Ser Arg Val Glu Gly Arg Arg Arg Ala Asn Glu Asn
305                 310                 315                 320

Ser Asn Ile Gln Leu Pro Tyr Asp Ser Arg Trp Glu Phe Pro Arg Asp
                325                 330                 335

Gly Leu Val Leu Gly Arg Val Leu Gly Ser Gly Ala Phe Gly Lys Val
            340                 345                 350

Val Glu Gly Thr Ala Tyr Gly Leu Ser Arg Ser Gln Pro Val Met Lys
        355                 360                 365

Val Ala Val Lys Met Leu Lys Pro Thr Ala Arg Ser Ser Glu Lys Gln
    370                 375                 380

Ala Leu Met Ser Glu Leu Lys Ile Met Thr His Leu Gly Pro His Leu
385                 390                 395                 400

Asn Ile Val Asn Leu Leu Gly Ala Cys Thr Lys Ser Gly Pro Ile Tyr
                405                 410                 415

Ile Ile Thr Glu Tyr Cys Phe Tyr Gly Asp Leu Val Asn Tyr Leu His
            420                 425                 430

Lys Asn Arg Asp Ser Phe Leu Ser His His Pro Glu Lys Pro Lys Lys
        435                 440                 445

Glu Leu Asp Ile Phe Gly Leu Asn Pro Ala Asp Glu Ser Thr Arg Ser
    450                 455                 460
```

-continued

```
Tyr Val Ile Leu Ser Phe Glu Asn Asn Gly Asp Tyr Met Asp Met Lys
465                 470                 475                 480

Gln Ala Asp Thr Thr Gln Tyr Val Pro Met Leu Glu Arg Lys Glu Val
                485                 490                 495

Ser Lys Tyr Ser Asp Ile Gln Arg Ser Leu Tyr Asp Arg Pro Ala Ser
            500                 505                 510

Tyr Lys Lys Lys Ser Met Leu Asp Ser Glu Val Lys Asn Leu Leu Ser
        515                 520                 525

Asp Asp Asn Ser Glu Gly Leu Thr Leu Leu Asp Leu Leu Ser Phe Thr
    530                 535                 540

Tyr Gln Val Ala Arg Gly Met Glu Phe Leu Ala Ser Lys Asn Cys Val
545                 550                 555                 560

His Arg Asp Leu Ala Ala Arg Asn Val Leu Leu Ala Gln Gly Lys Ile
                565                 570                 575

Val Lys Ile Cys Asp Phe Gly Leu Ala Arg Asp Ile Met His Asp Ser
            580                 585                 590

Asn Tyr Val Ser Lys Gly Ser Thr Phe Leu Pro Val Lys Trp Met Ala
        595                 600                 605

Pro Glu Ser Ile Phe Asp Asn Leu Tyr Thr Thr Leu Ser Asp Val Trp
    610                 615                 620

Ser Tyr Gly Ile Leu Leu Trp Glu Ile Phe Ser Leu Gly Gly Thr Pro
625                 630                 635                 640

Tyr Pro Gly Met Met Val Asp Ser Thr Phe Tyr Asn Lys Ile Lys Ser
                645                 650                 655

Gly Tyr Arg Met Ala Lys Pro Asp His Ala Thr Ser Glu Val Tyr Glu
            660                 665                 670

Ile Met Val Lys Cys Trp Asn Ser Glu Pro Glu Lys Arg Pro Ser Phe
        675                 680                 685

Tyr His Leu Ser Glu Ile Val Glu Asn Leu Leu Pro Gly Gln Tyr Lys
    690                 695                 700

Lys Ser Tyr Glu Lys Ile His Leu Asp Phe Leu Lys Ser Asp His Pro
705                 710                 715                 720

Ala Val Ala Arg Met Arg Val Asp Ser Asp Asn Ala Tyr Ile Gly Val
                725                 730                 735

Thr Tyr Lys Asn Glu Glu Asp Lys Leu Lys Asp Trp Glu Gly Gly Leu
            740                 745                 750

Asp Glu Gln Arg Leu Ser Ala Asp Ser Gly Tyr Ile Ile Pro Leu Pro
        755                 760                 765

Asp Ile Asp Pro Val Pro Glu Glu Glu Asp Leu Gly Lys Arg Asn Arg
    770                 775                 780

His Ser Ser Gln Thr Ser Glu Glu Ser Ala Ile Glu Thr Gly Ser Ser
785                 790                 795                 800

Ser Ser Thr Phe Ile Lys Arg Glu Asp Glu Thr Ile Glu Asp Ile Asp
                805                 810                 815

Met Met Asp Asp Ile Gly Ile Asp Ser Ser Asp Leu Val Glu Asp Ser
            820                 825                 830

Phe Leu


<210> SEQ ID NO 3
<211> LENGTH: 826
<212> TYPE: PRT
<213> ORGANISM: homo sapiens
```

-continued

<400> SEQUENCE: 3

```
Met Ser Ala Gly Glu Val Glu Arg Leu Val Ser Glu Leu Ser Gly Gly
 1               5                  10                  15

Thr Gly Gly Asp Glu Glu Glu Glu Trp Leu Tyr Gly Gly Pro Trp Asp
            20                  25                  30

Val His Val His Ser Asp Leu Ala Lys Asp Leu Asp Glu Asn Glu Val
        35                  40                  45

Glu Arg Pro Glu Glu Glu Asn Ala Ser Ala Asn Pro Pro Ser Gly Ile
    50                  55                  60

Glu Asp Glu Thr Ala Glu Asn Gly Val Pro Lys Pro Lys Val Thr Glu
65                  70                  75                  80

Thr Glu Asp Asp Ser Asp Ser Asp Ser Asp Asp Asp Glu Asp Asp Val
                85                  90                  95

His Val Thr Ile Gly Asp Ile Lys Thr Gly Ala Pro Gln Tyr Gly Ser
            100                 105                 110

Tyr Gly Thr Ala Pro Val Asn Leu Asn Ile Lys Thr Gly Gly Arg Val
        115                 120                 125

Tyr Gly Thr Thr Gly Thr Lys Val Lys Gly Val Asp Leu Asp Ala Pro
    130                 135                 140

Gly Ser Ile Asn Gly Val Pro Leu Leu Glu Val Asp Leu Asp Ser Phe
145                 150                 155                 160

Glu Asp Lys Pro Trp Arg Lys Pro Gly Ala Asp Leu Ser Asp Tyr Phe
                165                 170                 175

Asn Tyr Gly Phe Asn Glu Asp Thr Trp Lys Ala Tyr Cys Glu Lys Gln
            180                 185                 190

Lys Arg Ile Arg Met Gly Leu Glu Val Ile Pro Val Thr Ser Thr Thr
        195                 200                 205

Asn Lys Ile Thr Val Gln Gln Gly Arg Thr Gly Asn Ser Glu Lys Glu
    210                 215                 220

Thr Ala Leu Pro Ser Thr Lys Ala Glu Phe Thr Ser Pro Pro Ser Leu
225                 230                 235                 240

Phe Lys Thr Gly Leu Pro Pro Ser Arg Asn Ser Thr Ser Ser Gln Ser
                245                 250                 255

Gln Thr Ser Thr Ala Ser Arg Lys Ala Asn Ser Ser Val Gly Lys Trp
            260                 265                 270

Gln Asp Arg Tyr Gly Arg Ala Glu Ser Pro Asp Leu Arg Arg Leu Pro
        275                 280                 285

Gly Ala Ile Asp Val Ile Gly Gln Thr Ile Thr Ile Ser Arg Val Glu
    290                 295                 300

Gly Arg Arg Arg Ala Asn Glu Asn Ser Asn Ile Gln Leu Pro Tyr Asp
305                 310                 315                 320

Ser Arg Trp Glu Phe Pro Arg Asp Gly Leu Val Leu Gly Arg Val Leu
                325                 330                 335

Gly Ser Gly Ala Phe Gly Lys Val Val Glu Gly Thr Ala Tyr Gly Leu
            340                 345                 350

Ser Arg Ser Gln Pro Val Met Lys Val Ala Val Lys Met Leu Lys Pro
        355                 360                 365

Thr Ala Arg Ser Ser Glu Lys Gln Ala Leu Met Ser Glu Leu Lys Ile
    370                 375                 380

Met Thr His Leu Gly Pro His Leu Asn Ile Val Asn Leu Leu Gly Ala
385                 390                 395                 400

Cys Thr Lys Ser Gly Pro Ile Tyr Ile Ile Thr Glu Tyr Cys Phe Tyr
                405                 410                 415
```

-continued

```
Gly Asp Leu Val Asn Tyr Leu His Lys Asn Arg Asp Ser Phe Leu Ser
            420                 425                 430

His His Pro Glu Lys Pro Lys Lys Glu Leu Asp Ile Phe Gly Leu Asn
        435                 440                 445

Pro Ala Asp Glu Ser Thr Arg Ser Tyr Val Ile Leu Ser Phe Glu Asn
    450                 455                 460

Asn Gly Asp Tyr Met Asp Met Lys Gln Ala Asp Thr Thr Gln Tyr Val
465                 470                 475                 480

Pro Met Leu Glu Arg Lys Glu Val Ser Lys Tyr Ser Asp Ile Gln Arg
                485                 490                 495

Ser Leu Tyr Asp Arg Pro Ala Ser Tyr Lys Lys Lys Ser Met Leu Asp
            500                 505                 510

Ser Glu Val Lys Asn Leu Leu Ser Asp Asp Asn Ser Glu Gly Leu Thr
        515                 520                 525

Leu Leu Asp Leu Leu Ser Phe Thr Tyr Gln Val Ala Arg Gly Met Glu
    530                 535                 540

Phe Leu Ala Ser Lys Asn Cys Val His Arg Asp Leu Ala Ala Arg Asn
545                 550                 555                 560

Val Leu Leu Ala Gln Gly Lys Ile Val Lys Ile Cys Asp Phe Gly Leu
                565                 570                 575

Ala Arg Asp Ile Met His Asp Ser Asn Tyr Val Ser Lys Gly Ser Thr
            580                 585                 590

Phe Leu Pro Val Lys Trp Met Ala Pro Glu Ser Ile Phe Asp Asn Leu
        595                 600                 605

Tyr Thr Thr Leu Ser Asp Val Trp Ser Tyr Gly Ile Leu Leu Trp Glu
    610                 615                 620

Ile Phe Ser Leu Gly Gly Thr Pro Tyr Pro Gly Met Met Val Asp Ser
625                 630                 635                 640

Thr Phe Tyr Asn Lys Ile Lys Ser Gly Tyr Arg Met Ala Lys Pro Asp
                645                 650                 655

His Ala Thr Ser Glu Val Tyr Glu Ile Met Val Lys Cys Trp Asn Ser
            660                 665                 670

Glu Pro Glu Lys Arg Pro Ser Phe Tyr His Leu Ser Glu Ile Val Glu
        675                 680                 685

Asn Leu Leu Pro Gly Gln Tyr Lys Lys Ser Tyr Glu Lys Ile His Leu
    690                 695                 700

Asp Phe Leu Lys Ser Asp His Pro Ala Val Ala Arg Met Arg Val Asp
705                 710                 715                 720

Ser Asp Asn Ala Tyr Ile Gly Val Thr Tyr Lys Asn Glu Glu Asp Lys
                725                 730                 735

Leu Lys Asp Trp Glu Gly Gly Leu Asp Glu Gln Arg Leu Ser Ala Asp
            740                 745                 750

Ser Gly Tyr Ile Ile Pro Leu Pro Asp Ile Asp Pro Val Pro Glu Glu
        755                 760                 765

Glu Asp Leu Gly Lys Arg Asn Arg His Ser Ser Gln Thr Ser Glu Glu
    770                 775                 780

Ser Ala Ile Glu Thr Gly Ser Ser Ser Ser Thr Phe Ile Lys Arg Glu
785                 790                 795                 800

Asp Glu Thr Ile Glu Asp Ile Asp Met Met Asp Asp Ile Gly Ile Asp
                805                 810                 815

Ser Ser Asp Leu Val Glu Asp Ser Phe Leu
            820                 825
```

-continued

```
<210> SEQ ID NO 4
<211> LENGTH: 811
<212> TYPE: PRT
<213> ORGANISM: homo sapiens

<400> SEQUENCE: 4

Met Ser Ala Gly Glu Val Glu Arg Leu Val Ser Glu Leu Ser Gly Gly
 1               5                  10                  15

Thr Gly Gly Asp Glu Glu Glu Glu Trp Leu Tyr Gly Asp Glu Asn Glu
            20                  25                  30

Val Glu Arg Pro Glu Glu Glu Asn Ala Ser Ala Asn Pro Pro Ser Gly
        35                  40                  45

Ile Glu Asp Glu Thr Ala Glu Asn Gly Val Pro Lys Pro Lys Val Thr
    50                  55                  60

Glu Thr Glu Asp Asp Ser Asp Ser Asp Ser Asp Asp Asp Glu Asp Asp
65                  70                  75                  80

Val His Val Thr Ile Gly Asp Ile Lys Thr Gly Ala Pro Gln Tyr Gly
                85                  90                  95

Ser Tyr Gly Thr Ala Pro Val Asn Leu Asn Ile Lys Thr Gly Gly Arg
            100                 105                 110

Val Tyr Gly Thr Thr Gly Thr Lys Val Lys Gly Val Asp Leu Asp Ala
        115                 120                 125

Pro Gly Ser Ile Asn Gly Val Pro Leu Leu Glu Val Asp Leu Asp Ser
    130                 135                 140

Phe Glu Asp Lys Pro Trp Arg Lys Pro Gly Ala Asp Leu Ser Asp Tyr
145                 150                 155                 160

Phe Asn Tyr Gly Phe Asn Glu Asp Thr Trp Lys Ala Tyr Cys Glu Lys
                165                 170                 175

Gln Lys Arg Ile Arg Met Gly Leu Glu Val Ile Pro Val Thr Ser Thr
            180                 185                 190

Thr Asn Lys Ile Thr Val Gln Gln Gly Arg Thr Gly Asn Ser Glu Lys
        195                 200                 205

Glu Thr Ala Leu Pro Ser Thr Lys Ala Glu Phe Thr Ser Pro Pro Ser
    210                 215                 220

Leu Phe Lys Thr Gly Leu Pro Pro Ser Arg Asn Ser Thr Ser Ser Gln
225                 230                 235                 240

Ser Gln Thr Ser Thr Ala Ser Arg Lys Ala Asn Ser Ser Val Gly Lys
                245                 250                 255

Trp Gln Asp Arg Tyr Gly Arg Ala Glu Ser Pro Asp Leu Arg Arg Leu
            260                 265                 270

Pro Gly Ala Ile Asp Val Ile Gly Gln Thr Ile Thr Ile Ser Arg Val
        275                 280                 285

Glu Gly Arg Arg Arg Ala Asn Glu Asn Ser Asn Ile Gln Leu Pro Tyr
    290                 295                 300

Asp Ser Arg Trp Glu Phe Pro Arg Asp Gly Leu Val Leu Gly Arg Val
305                 310                 315                 320

Leu Gly Ser Gly Ala Phe Gly Lys Val Val Glu Gly Thr Ala Tyr Gly
                325                 330                 335

Leu Ser Arg Ser Gln Pro Val Met Lys Val Ala Val Lys Met Leu Lys
            340                 345                 350

Pro Thr Ala Arg Ser Ser Glu Lys Gln Ala Leu Met Ser Glu Leu Lys
        355                 360                 365

Ile Met Thr His Leu Gly Pro His Leu Asn Ile Val Asn Leu Leu Gly
    370                 375                 380
```

-continued

Ala Cys Thr Lys Ser Gly Pro Ile Tyr Ile Ile Thr Glu Tyr Cys Phe
385 390 395 400

Tyr Gly Asp Leu Val Asn Tyr Leu His Lys Asn Arg Asp Ser Phe Leu
405 410 415

Ser His His Pro Glu Lys Pro Lys Lys Glu Leu Asp Ile Phe Gly Leu
420 425 430

Asn Pro Ala Asp Glu Ser Thr Arg Ser Tyr Val Ile Leu Ser Phe Glu
435 440 445

Asn Asn Gly Asp Tyr Met Asp Met Lys Gln Ala Asp Thr Thr Gln Tyr
450 455 460

Val Pro Met Leu Glu Arg Lys Glu Val Ser Lys Tyr Ser Asp Ile Gln
465 470 475 480

Arg Ser Leu Tyr Asp Arg Pro Ala Ser Tyr Lys Lys Lys Ser Met Leu
485 490 495

Asp Ser Glu Val Lys Asn Leu Leu Ser Asp Asp Asn Ser Glu Gly Leu
500 505 510

Thr Leu Leu Asp Leu Leu Ser Phe Thr Tyr Gln Val Ala Arg Gly Met
515 520 525

Glu Phe Leu Ala Ser Lys Asn Cys Val His Arg Asp Leu Ala Ala Arg
530 535 540

Asn Val Leu Leu Ala Gln Gly Lys Ile Val Lys Ile Cys Asp Phe Gly
545 550 555 560

Leu Ala Arg Asp Ile Met His Asp Ser Asn Tyr Val Ser Lys Gly Ser
565 570 575

Thr Phe Leu Pro Val Lys Trp Met Ala Pro Glu Ser Ile Phe Asp Asn
580 585 590

Leu Tyr Thr Thr Leu Ser Asp Val Trp Ser Tyr Gly Ile Leu Leu Trp
595 600 605

Glu Ile Phe Ser Leu Gly Gly Thr Pro Tyr Pro Gly Met Met Val Asp
610 615 620

Ser Thr Phe Tyr Asn Lys Ile Lys Ser Gly Tyr Arg Met Ala Lys Pro
625 630 635 640

Asp His Ala Thr Ser Glu Val Tyr Glu Ile Met Val Lys Cys Trp Asn
645 650 655

Ser Glu Pro Glu Lys Arg Pro Ser Phe Tyr His Leu Ser Glu Ile Val
660 665 670

Glu Asn Leu Leu Pro Gly Gln Tyr Lys Lys Ser Tyr Glu Lys Ile His
675 680 685

Leu Asp Phe Leu Lys Ser Asp His Pro Ala Val Ala Arg Met Arg Val
690 695 700

Asp Ser Asp Asn Ala Tyr Ile Gly Val Thr Tyr Lys Asn Glu Glu Asp
705 710 715 720

Lys Leu Lys Asp Trp Glu Gly Gly Leu Asp Glu Gln Arg Leu Ser Ala
725 730 735

Asp Ser Gly Tyr Ile Ile Pro Leu Pro Asp Ile Asp Pro Val Pro Glu
740 745 750

Glu Glu Asp Leu Gly Lys Arg Asn Arg His Ser Ser Gln Thr Ser Glu
755 760 765

Glu Ser Ala Ile Glu Thr Gly Ser Ser Ser Ser Thr Phe Ile Lys Arg
770 775 780

-continued

```
Glu Asp Glu Thr Ile Glu Asp Ile Asp Met Met Asp Asp Ile Gly Ile
785                 790                 795                 800

Asp Ser Ser Asp Leu Val Glu Asp Ser Phe Leu
                805                 810
```

```
<210> SEQ ID NO 5
<211> LENGTH: 2541
<212> TYPE: DNA
<213> ORGANISM: homo sapiens

<400> SEQUENCE: 5

atgtcggccg gcgaggtcga gcgcctagtg tcggagctga gcggcgggac cggaggggat      60

gaggaggaag agtggctcta tggcggccca tgggacgtgc atgtgcacag tgatttggca     120

aaggacctag atgaaaatga agttgaaagg ccagaagaag aaaatgccag tgctaatcct     180

ccatctggaa ttgaagatga aactgctgaa aatggtgtac caaaaccgaa agtgactgag     240

accgaagatg atagtgatag tgacagcgat gatgatgaag atgatgttca tgtcactata     300

ggagacatta aaacgggagc accacagtat gggagttatg gtacagcacc tgtaaatctt     360

aacatcaaga caggggggaag agtttatgga actacaggga caaaagtcaa aggagtagac     420

cttgatgcac ctggaagcat taatggagtt ccactcttag aggtagattt ggattctttt     480

gaagataaac catggcgtaa acctggtgct gatctttctg attattttaa ttatgggttt     540

aatgaagata cctggaaagc ttactgtgaa aaacaaaaga ggatacgaat gggacttgaa     600

gttataccag taacctctac tacaaataaa attacggccg aagactgtac tatggaagtt     660

acaccaggtg cagagatcca agatggcaga ttcaatcttt ttaaggtaca gcagggaaga     720

actggaaact cagagaaaga aactgccctt ccatctacaa aagctgagtt tacttctcct     780

ccttctttgt tcaagactgg gcttccaccg agcagaaaca gcacttcttc tcagtctcag     840

acaagtactg cctccagaaa agccaattca agcgttggga agtggcagga tcgatatggg     900

agggccgaat cacctgatct aaggagatta cctggggcaa ttgatgttat cggtcagact     960

ataactatca gccgagtaga aggcaggcga cgggcaaatg agaacagcaa catacaggac    1020

tcaagatggg agtttccaag agatggacta gtgcttggtc gggtcttggg gtctggagcg    1080

tttgggaagg tggttgaagg aacagcctat ggattaagcc ggtcccaacc tgtcatgaaa    1140

gttgcagtga agatgctaaa acccacggcc agatccagtg aaaaacaagc tctcatgtct    1200

gaactgaaga taatgactca cctggggcca catttgaaca ttgtaaactt gctgggagcc    1260

tgcaccaagt caggccccat ttacatcatc acagagtatt gcttctatgg agatttggtc    1320

aactatttgc ataagaatag ggatagcttc ctgagccacc acccagagaa gccaaagaaa    1380

gagctggata tctttggatt gaaccctgct gatgaaagca cacggagcta tgttatttta    1440

tcttttgaaa acaatggtga ctacatggac atgaagcagg ctgatactac acagtatgtc    1500

cccatgctag aaaggaaaga ggtttctaaa tattccgaca tccagagatc actctatgat    1560

cgtccagcct catataagaa gaaatctatg ttagactcag aagtcaaaaa cctcctttca    1620

gatgataact cagaaggcct tactttattg gatttgttga gcttcaccta tcaagttgcc    1680

cgaggaatgg agtttttggc ttcaaaaaat tgtgtccacc gtgatctggc tgctcgcaac    1740

gttctcctgg cacaaggaaa aattgtgaag atctgtgact ttggcctggc cagagacatc    1800

atgcatgatt cgaactatgt gtcgaaaggc agtacctttc tgcccgtgaa gtggatggct    1860

cctgagagca tctttgacaa cctctacacc acactgagtg atgtctggtc ttatggcatt    1920

ctgctctggg agatcttttc ccttggtggc acccccttacc ccggcatgat ggtggattct    1980
```

-continued

```
actttctaca ataagatcaa gagtgggtac cggatggcca agcctgacca cgctaccagt   2040
gaagtctacg agatcatggt gaaatgctgg aacagtgagc cggagaagag accctccttt   2100
taccacctga gtgagattgt ggagaatctg ctgcctggac aatataaaaa gagttatgaa   2160
aaaattcacc tggacttcct gaagagtgac catcctgctg tggcacgcat gcgtgtggac   2220
tcagacaatg catacattgg tgtcacctac aaaaacgagg aagacaagct gaaggactgg   2280
gagggtggtc tggatgagca gagactgagc gctgacagtg gctacatcat tcctctgcct   2340
gacattgacc ctgtccctga ggaggaggac ctgggcaaga ggaacagaca cagctcgcag   2400
acctctgaag agagtgccat tgagacgggt tccagcagtt ccaccttcat caagagagag   2460
gacgagacca ttgaagacat cgacatgatg gacgacatcg gcatagactc ttcagacctg   2520
gtggaagaca gcttcctgta a                                              2541
```

<210> SEQ ID NO 6
<211> LENGTH: 2496
<212> TYPE: DNA
<213> ORGANISM: homo sapiens

<400> SEQUENCE: 6

```
atgtcggccg gcgaggtcga gcgcctagtg tcggagctga gcggcgggac cggaggggat     60
gaggaggaag agtggctcta tggcgatgaa aatgaagttg aaaggccaga agaagaaaat    120
gccagtgcta atcctccatc tggaattgaa gatgaaactg ctgaaaatgg tgtaccaaaa    180
ccgaaagtga ctgagaccga agatgatagt gatagtgaca gcgatgatga tgaagatgat    240
gttcatgtca ctataggaga cattaaaacg ggagcaccac agtatgggag ttatggtaca    300
gcacctgtaa atcttaacat caagacaggg ggaagagttt atggaactac agggacaaaa    360
gtcaaaggag tagaccttga tgcacctgga agcattaatg gagttccact cttagaggta    420
gatttggatt cttttgaaga taaaccatgg cgtaaacctg gtgctgatct ttctgattat    480
tttaattatg ggtttaatga agatacctgg aaagcttact gtgaaaaaca aaagaggata    540
cgaatgggac ttgaagttat accagtaacc tctactacaa ataaaattac ggccgaagac    600
tgtactatgg aagttacacc aggtgcagag atccaagatg gcagattcaa tctttttaag    660
gtacagcagg gaagaactgg aaactcagag aaagaaactg cccttccatc tacaaaagct    720
gagtttactt ctcctccttc tttgttcaag actgggcttc caccgagcag aaacagcact    780
tcttctcagt ctcagacaag tactgcctcc agaaaagcca attcaagcgt tgggaagtgg    840
caggatcgat atgggagggc cgaatcacct gatctaagga gattacctgg ggcaattgat    900
gttatcggtc agactataac tatcagccga gtagaaggca ggcgacgggc aaatgagaac    960
agcaacatac aggactcaag atgggagttt ccaagagatg gactagtgct tggtcgggtc   1020
ttggggtctg gagcgtttgg gaaggtggtt gaaggaacag cctatggatt aagccggtcc   1080
caacctgtca tgaaagttgc agtgaagatg ctaaaaccca cggccagatc cagtgaaaaa   1140
caagctctca tgtctgaact gaagataatg actcacctgg ggccacattt gaacattgta   1200
aacttgctgg gagcctgcac caagtcaggc cccatttaca tcatcacaga gtattgcttc   1260
tatggagatt tggtcaacta tttgcataag aatagggata gcttcctgag ccaccaccca   1320
gagaagccaa agaaagagct ggatatcttt ggattgaacc ctgctgatga aagcacacgg   1380
agctatgtta ttttatcttt tgaaaacaat ggtgactaca tggacatgaa gcaggctgat   1440
actacacagt atgtccccat gctagaaagg aaagaggttt ctaaatattc cgacatccag   1500
agatcactct atgatcgtcc agcctcatat aagaagaaat ctatgttaga ctcagaagtc   1560
```

-continued

```
aaaaacctcc tttcagatga taactcagaa ggccttactt tattggattt gttgagcttc   1620

acctatcaag ttgcccgagg aatggagttt ttggcttcaa aaaattgtgt ccaccgtgat   1680

ctggctgctc gcaacgttct cctggcacaa ggaaaaattg tgaagatctg tgactttggc   1740

ctggccagag acatcatgca tgattcgaac tatgtgtcga aaggcagtac ctttctgccc   1800

gtgaagtgga tggctcctga gagcatcttt gacaacctct acaccacact gagtgatgtc   1860

tggtcttatg gcattctgct ctgggagatc ttttcccttg gtggcacccc ttaccccggc   1920

atgatggtgg attctacttt ctacaataag atcaagagtg ggtaccggat ggccaagcct   1980

gaccacgcta ccagtgaagt ctacgagatc atggtgaaat gctggaacag tgagccggag   2040

aagagaccct ccttttacca cctgagtgag attgtggaga atctgctgcc tggacaatat   2100

aaaaagagtt atgaaaaaat tcacctggac ttcctgaaga gtgaccatcc tgctgtggca   2160

cgcatgcgtg tggactcaga caatgcatac attggtgtca cctacaaaaa cgaggaagac   2220

aagctgaagg actgggaggg tggtctggat gagcagagac tgagcgctga cagtggctac   2280

atcattcctc tgcctgacat tgaccctgtc cctgaggagg aggacctggg caagaggaac   2340

agacacagct cgcagacctc tgaagagagt gccattgaga cgggttccag cagttccacc   2400

ttcatcaaga gagaggacga gaccattgaa gacatcgaca tgatggacga catcggcata   2460

gactcttcag acctggtgga agacagcttc ctgtaa                             2496
```

<210> SEQ ID NO 7
<211> LENGTH: 2472
<212> TYPE: DNA
<213> ORGANISM: homo sapiens

<400> SEQUENCE: 7

```
atgtcggccg gcgaggtcga gcgcctagtg tcggagctga gcggcgggac cggaggggat     60

gaggaggaag agtggctcta tggcggccca tgggacgtgc atgtgcacag tgatttggca    120

aaggacctag atgaaaatga agttgaaagg ccagaagaag aaaatgccag tgctaatcct    180

ccatctggaa ttgaagatga aactgctgaa aatggtgtac caaaaccgaa agtgactgag    240

accgaagatg atagtgatag tgacagcgat gatgatgaag atgatgttca tgtcactata    300

ggagacatta aaacgggagc accacagtat gggagttatg gtacagcacc tgtaaatctt    360

aacatcaaga caggggggaag agtttatgga actacaggga caaaagtcaa aggagtagac    420

cttgatgcac ctggaagcat taatggagtt ccactcttag aggtagattt ggattctttt    480

gaagataaac catggcgtaa acctggtgct gatctttctg attattttaa ttatgggttt    540

aatgaagata cctggaaagc ttactgtgaa aaacaaaaga ggatacgaat gggacttgaa    600

gttataccag taacctctac tacaaataaa attacggtac agcagggaag aactggaaac    660

tcagagaaag aaactgccct tccatctaca aaagctgagt ttacttctcc tccttctttg    720

ttcaagactg ggcttccacc gagcagaaac agcacttctt ctcagtctca gacaagtact    780

gcctccagaa aagccaattc aagcgttggg aagtggcagg atcgatatgg gagggccgaa    840

tcacctgatc taaggagatt acctggggca attgatgtta tcggtcagac tataactatc    900

agccgagtag aaggcaggcg acgggcaaat gagaacagca acatacagga ctcaagatgg    960

gagtttccaa gagatggact agtgcttggt cgggtcttgg ggtctggagc gtttgggaag   1020

gtggttgaag gaacagccta tggattaagc cggtcccaac ctgtcatgaa agttgcagtg   1080

aagatgctaa aacccacggc cagatccagt gaaaaacaag ctctcatgtc tgaactgaag   1140

ataatgactc acctggggcc acatttgaac attgtaaact tgctgggagc ctgcaccaag   1200
```

```
tcaggcccca tttacatcat cacagagtat tgcttctatg gagatttggt caactatttg   1260

cataagaata gggatagctt cctgagccac cacccagaga agccaaagaa agagctggat   1320

atctttggat tgaaccctgc tgatgaaagc acacggagct atgttatttt atcttttgaa   1380

aacaatggtg actacatgga catgaagcag gctgatacta cacagtatgt ccccatgcta   1440

gaaaggaaag aggtttctaa atattccgac atccagagat cactctatga tcgtccagcc   1500

tcatataaga agaaatctat gttagactca gaagtcaaaa acctcctttc agatgataac   1560

tcagaaggcc ttactttatt ggatttgttg agcttcacct atcaagttgc ccgaggaatg   1620

gagtttttgg cttcaaaaaa ttgtgtccac cgtgatctgg ctgctcgcaa cgttctcctg   1680

gcacaaggaa aaattgtgaa gatctgtgac tttggcctgg ccagagacat catgcatgat   1740

tcgaactatg tgtcgaaagg cagtaccttt ctgcccgtga agtggatggc tcctgagagc   1800

atctttgaca acctctacac cacactgagt gatgtctggt cttatggcat tctgctctgg   1860

gagatctttt cccttggtgg caccccttac cccggcatga tggtggattc tactttctac   1920

aataagatca agagtgggta ccggatggcc aagcctgacc acgctaccag tgaagtctac   1980

gagatcatgg tgaaatgctg gaacagtgag ccggagaaga gaccctcctt ttaccacctg   2040

agtgagattg tggagaatct gctgcctgga caatataaaa agagttatga aaaaattcac   2100

ctggacttcc tgaagagtga ccatcctgct gtggcacgca tgcgtgtgga ctcagacaat   2160

gcatacattg gtgtcaccta caaaaacgag gaagacaagc tgaaggactg ggagggtggt   2220

ctggatgagc agagactgag cgctgacagt ggctacatca ttcctctgcc tgacattgac   2280

cctgtccctg aggaggagga cctgggcaag aggaacagac acagctcgca gacctctgaa   2340

gagagtgcca ttgagacggg ttccagcagt tccaccttca tcaagagaga ggacgagacc   2400

attgaagaca tcgacatgat ggacgacatc ggcatagact cttcagacct ggtggaagac   2460

agcttcctgt aa                                                       2472
```

<210> SEQ ID NO 8
<211> LENGTH: 2427
<212> TYPE: DNA
<213> ORGANISM: homo sapiens

<400> SEQUENCE: 8

```
atgtcggccg gcgaggtcga gcgcctagtg tcggagctga gcggcgggac cggaggggat     60

gaggaggaag agtggctcta tggcgatgaa aatgaagttg aaaggccaga agaagaaaat    120

gccagtgcta atcctccatc tggaattgaa gatgaaactg ctgaaaatgg tgtaccaaaa    180

ccgaaagtga ctgagaccga agatgatagt gatagtgaca gcgatgatga tgaagatgat    240

gttcatgtca ctataggaga cattaaaacg ggagcaccac agtatgggag ttatggtaca    300

gcacctgtaa atcttaacat caagacaggg ggaagagttt atggaactac agggacaaaa    360

gtcaaaggag tagaccttga tgcacctgga agcattaatg gagttccact cttagaggta    420

gatttggatt cttttgaaga taaaccatgg cgtaaacctg gtgctgatct ttctgattat    480

tttaattatg ggtttaatga agatacctgg aaagcttact gtgaaaaaca aaagaggata    540

cgaatgggac ttgaagttat accagtaacc tctactacaa ataaaattac ggtacagcag    600

ggaagaactg gaaactcaga gaaagaaact gcccttccat ctacaaaagc tgagtttact    660

tctcctcctt ctttgttcaa gactgggctt ccaccgagca gaaacagcac ttcttctcag    720

tctcagacaa gtactgcctc cagaaaagcc aattcaagcg ttgggaagtg gcaggatcga    780

tatgggaggg ccgaatcacc tgatctaagg agattacctg ggcaattgga tgttatcggt    840
```

-continued

```
cagactataa ctatcagccg agtagaaggc aggcgacggg caaatgagaa cagcaacata    900

caggactcaa gatgggagtt tccaagagat ggactagtgc ttggtcgggt cttggggtct    960

ggagcgtttg ggaaggtggt tgaaggaaca gcctatggat taagccggtc ccaacctgtc   1020

atgaaagttg cagtgaagat gctaaaaccc acggccagat ccagtgaaaa acaagctctc   1080

atgtctgaac tgaagataat gactcacctg ggccacatt  tgaacattgt aaacttgctg   1140

ggagcctgca ccaagtcagg ccccatttac atcatcacag agtattgctt ctatggagat   1200

ttggtcaact atttgcataa gaatagggat agcttcctga gccaccaccc agagaagcca   1260

aagaaagagc tggatatctt tggattgaac cctgctgatg aaagcacacg gagctatgtt   1320

attttatctt ttgaaaacaa tggtgactac atggacatga agcaggctga tactacacag   1380

tatgtcccca tgctagaaag gaaagaggtt tctaaatatt ccgacatcca gagatcactc   1440

tatgatcgtc cagcctcata taagaagaaa tctatgttag actcagaagt caaaaacctc   1500

ctttcagatg ataactcaga aggccttact ttattggatt tgttgagctt cacctatcaa   1560

gttgcccgag gaatggagtt tttggcttca aaaaattgtg tccaccgtga tctggctgct   1620

cgcaacgttc tcctggcaca aggaaaaatt gtgaagatct gtgactttgg cctggccaga   1680

gacatcatgc atgattcgaa ctatgtgtcg aaaggcagta cctttctgcc cgtgaagtgg   1740

atggctcctg agagcatctt tgacaacctc tacaccacac tgagtgatgt ctggtcttat   1800

ggcattctgc tctgggagat cttttccctt ggtggcaccc cttaccccgg catgatggtg   1860

gattctactt tctacaataa gatcaagagt gggtaccgga tggccaagcc tgaccacgct   1920

accagtgaag tctacgagat catggtgaaa tgctggaaca gtgagccgga gaagagaccc   1980

tccttttacc acctgagtga gattgtggag aatctgctgc ctggacaata taaaaagagt   2040

tatgaaaaaa ttcacctgga cttcctgaag agtgaccatc ctgctgtggc acgcatgcgt   2100

gtggactcag acaatgcata cattggtgtc acctacaaaa acgaggaaga caagctgaag   2160

gactgggagg gtggtctgga tgagcagaga ctgagcgctg acagtggcta catcattcct   2220

ctgcctgaca ttgaccctgt ccctgaggag gaggacctgg gcaagaggaa cagacacagc   2280

tcgcagacct ctgaagagag tgccattgag acgggttcca gcagttccac cttcatcaag   2340

agagaggacg agaccattga agacatcgac atgatggacg acatcggcat agactcttca   2400

gacctggtgg aagacagctt cctgtaa                                       2427
```

<210> SEQ ID NO 9
<211> LENGTH: 1079
<212> TYPE: DNA
<213> ORGANISM: homo sapiens

<400> SEQUENCE: 9

```
ggagattacc tggggcaatt gatgttatcg gtcagactat aactatcagc cgagtagaag     60

gcaggcgacg ggcaaatgag aacagcaaca tacaggttta gtattttaaa ataaataatt    120

ttctttaact gaaggatgat atcaacatta taatttaatt tattcaatag atagtcatag    180

tgctatgctg tgttttaggt gatacaaaga gatttaaaat gtgaagccag tcatttatta    240

taaaggcatt tccagttaga atttataatc tctgaatctt tttttaatag ggtttctttt    300

cttttccttg gtagaaacat agtacaggtt gagtatctct tatctgaaat gcttgggacc    360

agaagtgtat cagattttga aatgtttgga ttttgaaatg ttcatacgta tgtaatctta    420

gagatgagac ccaagtctaa acatgaaatt tatgtttcat aaataagtta tttaatttgt    480

tataatgatt tgttaattta tgataatctt ttttcctttg gcaaccctga gtaaactgtg    540
```

-continued

```
tagtgggcct gagttttgat tgtgatccgt cacatgtgag gttgggtgtg gaattttcca    600

cttgtgataa aatgttgatg ctcaaaatgt ttcggatttt agagcatttc agatttcaga    660

tttttggatt aggaatactc aacttgtata taggtttact gaatgaaaaa taaaagacca    720

ccagtgattt taccacctaa agataaccac atctggtaca tctcttgata ctaagcaaaa    780

ttgggatact attataatta tatttctgtg tatacttttt tccccatcta aaattatcat    840

ttgtatgttt tcatattctt aaaatatgat taaaatatct tcatgatagc ttcattggat    900

aaatatacca tgatttattt aatgtgacat ttctggaggt ggcgtagagc tgctttgttt    960

ttaggtgaaa aattgagggg agataaatta tcagtaagtt ggataattaa tgttagaact   1020

ttaataactg agacttccag ctattcattt tggccatact ttttttcatt atttattcc    1079
```

<210> SEQ ID NO 10
<211> LENGTH: 770
<212> TYPE: DNA
<213> ORGANISM: homo sapiens

<400> SEQUENCE: 10

```
tggtttgaga gatggtactg cctatcccta aaatgaacca ggcagccctc acacttcccc     60

accagcagtg agagattcct ggctcagaca cagccacact accttgctgc ccctgtgcat    120

gtctgccagg aaactttca ttgtgcctct ctctcttgtc acgtagccct gcgttctgaa     180

ctcacggtgg ctgctgcagt cctggtgctg ttggtgattg tgatcatctc acttattgtc    240

ctggttgtca tttggaaaca ggtagatatt ttctcataaa actaaagatc tttgaagcca    300

atgagaacaa gcatagcaac ctagttcagt gcttggcaca gagaaggagc tcagcaatta    360

catgtggagt gaacgttgtt ggactctact gtgtccagtc actgtgctgc ttcagtgaag    420

ctctggtgca ctgggacttt ggtaattcac cagttacctg tcctggtcat ttatagaaac    480

cgaggtatga aattcgctgg agggtcattg aatcaatcag cccagatgga catgaatata    540

tttatgtgga cccgatgcag ctgccttatg actcaagatg ggagtttcca agagatggac    600

tagtgcttgg taagttccat ggggtaacct cccaagactc ccttttccct tgcacacaac    660

tttacaattt ataggccttg gcagaataga gatctgagct tgtgcttagt aagaactagg    720

caatggaaat ttgctttcag aaatacattt ctgtcttgac agtaagttaa               770
```

<210> SEQ ID NO 11
<211> LENGTH: 12
<212> TYPE: DNA
<213> ORGANISM: homo sapiens

<400> SEQUENCE: 11

```
atacaggttt ag                                                         12
```

<210> SEQ ID NO 12
<211> LENGTH: 18
<212> TYPE: DNA
<213> ORGANISM: homo sapiens

<400> SEQUENCE: 12

```
gacccgatgc agctgcct                                                   18
```

<210> SEQ ID NO 13
<211> LENGTH: 20
<212> TYPE: DNA
<213> ORGANISM: homo sapiens

<400> SEQUENCE: 13
tccgcattgc aataaagtgg 20

<210> SEQ ID NO 14
<211> LENGTH: 20
<212> TYPE: DNA
<213> ORGANISM: homo sapiens

<400> SEQUENCE: 14
gttgcgctcg gggcggccat 20

<210> SEQ ID NO 15
<211> LENGTH: 20
<212> TYPE: DNA
<213> ORGANISM: homo sapiens

<400> SEQUENCE: 15
ttctgaacgg gatccagagg 20

<210> SEQ ID NO 16
<211> LENGTH: 20
<212> TYPE: DNA
<213> ORGANISM: homo sapiens

<400> SEQUENCE: 16
ggatgtcgga atatttagaa 20

<210> SEQ ID NO 17
<211> LENGTH: 20
<212> TYPE: DNA
<213> ORGANISM: homo sapiens

<400> SEQUENCE: 17
gcagaaaggt actgcctttc 20

<210> SEQ ID NO 18
<211> LENGTH: 19
<212> TYPE: DNA
<213> ORGANISM: homo sapiens

<400> SEQUENCE: 18
aattatgggt ttaatgaag 19

<210> SEQ ID NO 19
<211> LENGTH: 19
<212> TYPE: DNA
<213> ORGANISM: homo sapiens

<400> SEQUENCE: 19
aactttcatg acaggttgg 19

<210> SEQ ID NO 20
<211> LENGTH: 25
<212> TYPE: DNA
<213> ORGANISM: homo sapiens

<400> SEQUENCE: 20
ttcttactaa gcacaagctc agatc 25

<210> SEQ ID NO 21
<211> LENGTH: 23
<212> TYPE: DNA
<213> ORGANISM: homo sapiens -continued

```
<400> SEQUENCE: 21

aagcatctaa ttaggtgaaa ctg                                    23


<210> SEQ ID NO 22
<211> LENGTH: 20
<212> TYPE: DNA
<213> ORGANISM: homo sapiens

<400> SEQUENCE: 22

cagggaagaa ctggaaactc                                        20
```